US010519088B2

(12) United States Patent
Bertin et al.

(10) Patent No.: US 10,519,088 B2
(45) Date of Patent: Dec. 31, 2019

(54) METHODS OF MAKING FUNCTIONALIZED INTERNAL OLEFINS AND USES THEREOF

(71) Applicant: Elevance Renewable Sciences, Inc., Woodridge, IL (US)

(72) Inventors: Paul A. Bertin, Woodridge, IL (US); Jordan R. Quinn, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 14/921,117

(22) Filed: Oct. 23, 2015

(65) Prior Publication Data

US 2016/0102037 A1  Apr. 14, 2016

Related U.S. Application Data

(63) Continuation of application No. 14/090,762, filed on Nov. 26, 2013, now abandoned.

(60) Provisional application No. 61/731,567, filed on Nov. 30, 2012.

(51) Int. Cl.
| | | |
|---|---|---|
| *C07C 51/09* | (2006.01) |
| *C07C 67/333* | (2006.01) |
| *C07C 67/475* | (2006.01) |
| *C07B 35/08* | (2006.01) |
| *C07C 5/25* | (2006.01) |
| *C07C 51/295* | (2006.01) |
| *C07C 51/34* | (2006.01) |
| *C07C 67/347* | (2006.01) |
| *C07C 1/26* | (2006.01) |
| *C07C 67/303* | (2006.01) |
| *C07C 67/00* | (2006.01) |

(52) U.S. Cl.
CPC .............. *C07C 51/09* (2013.01); *C07B 35/08* (2013.01); *C07C 1/26* (2013.01); *C07C 5/25* (2013.01); *C07C 5/2562* (2013.01); *C07C 51/295* (2013.01); *C07C 51/34* (2013.01); *C07C 67/00* (2013.01); *C07C 67/303* (2013.01); *C07C 67/333* (2013.01); *C07C 67/347* (2013.01); *C07C 67/475* (2013.01); *C07C 2531/24* (2013.01)

(58) Field of Classification Search
None
See application file for complete search history.

(56) References Cited

U.S. PATENT DOCUMENTS

| 3,351,566 A | 11/1967 | Taylor |
| 4,079,047 A | 3/1978 | Jackson, Jr. et al. |
| 5,162,485 A | 11/1992 | O'Dell et al. |
| 5,240,963 A | 8/1993 | Domb et al. |
| 5,864,049 A | 1/1999 | Dos Santos et al. |
| 6,846,772 B2 | 1/2005 | Lok et al. |

| 2007/0098619 A1 | 5/2007 | Harmer et al. |
| 2007/0100181 A1 | 5/2007 | Harmer et al. |
| 2009/0264672 A1* | 10/2009 | Abraham ............. B01J 31/2265 560/190 |
| 2010/0145086 A1 | 6/2010 | Schrodi et al. |
| 2010/0196973 A1 | 8/2010 | Dubois |
| 2010/0305354 A1 | 12/2010 | Dubois |
| 2011/0113679 A1 | 5/2011 | Cohen et al. |
| 2012/0071676 A1 | 3/2012 | Schrodi |
| 2013/0035502 A1* | 2/2013 | Cohen .................. C10G 29/205 560/129 |
| 2013/0085288 A1 | 4/2013 | Snead et al. |

FOREIGN PATENT DOCUMENTS

| EP | 0167201 | 1/1986 |
| EP | 0168091 | 1/1986 |
| FR | 2843110 | 2/2004 |
| SE | 133160 | 10/1951 |
| SE | 134616 | 2/2004 |
| WO | 2008140468 | 11/2008 |
| WO | 2009109857 | 9/2009 |

OTHER PUBLICATIONS

Ranganatian et al. Tetrahedron, 1980, vol. 36, 1869-1875.*
Int'l Search Report & Written Opinion, PCT App. No. PCT/US2013/071822, dated Dec. 25, 2013.
Chem. Rev., vol. 109, pp. 3211-3226 (2009).
Chem. Rev., vol. 102, pp. 145-179 (2002).
Domiguez et al., Ciencia, vol. 3-4, pp. 73-74 (1960).
Ellis et al., Biochem. J., vol. 46, pp. 129-141 (1950).
Feuell et al., J. Chem. Soc., pp. 3414-3418 (1954).
Katritzky et al., J. Am. Chem. Soc., vol. 47, pp. 3506-3511 (1982).
Dicarboxylic Acids, in Kirk-Othmer Ency. Chem. Tech., pp. 1-18 (2010).
Kobayashi et al., Receueil de Travaux, vol. 29, pp. 40-42 (1955).
Lim et al., J. Org. Chem., vol. 74, pp. 4565-4572 (2009).
Liu et al., J. Catalysis, vol. 242, pp. 278-286 (2006).
Metzger et al., Eu. J. Lipid Sci. Tech., vol. 111, pp. 865-876 (2009).
Moiseev et al., New J. Chem., pp. 1217-1227 (1998).
Morozov et al., Neft. Neft., vol. 2, pp. 36-28 (1977).
Neburchilov et al., J. Power Sources, vol. 169, pp. 221-238 (2007).
Ooi et al., J. Palm Oil Res, vol. 11, pp. 53-61 (1999).
Ranganathan et al., Tetrahedron, vol. 36, pp. 1869-1875 (1980).
Rup et al., Tetrahedron Lett., vol. 51, pp. 3123-3126 (2008).
Shibahara et al., J. Am. Oil Chem. Soc., vol. 85 (2008).
Verkade et al., Recueil de Travaux, vol. 46, pp. 200-207 (1927).
Wolff et al., 9th Int'l Elec. Cont. Synthetic Org. Chem., pp. 1-6 (2005).

(Continued)

*Primary Examiner* — Ana Z Muresan
(74) *Attorney, Agent, or Firm* — Kilpatrick Townsend & Stockton LLP

(57) ABSTRACT

A method of isomerizing methyl 9-decenoate in a reaction mixture, and forming methyl 8-decenoate, and reacting the methyl 8-decenoate by metathesis to form 1,16-dimethyl 8-hexadecenedioate, and hydrogenating 1,16-dimethyl 8-hexadecenedioate to form 1,16-dimethyl hexadecanedioate. In some embodiments, the 1,16-dimethyl hexadecanedioate can be converted to hexadecanedioic acid.

2 Claims, 8 Drawing Sheets

(56) References Cited

OTHER PUBLICATIONS

Zimmermann et al., Tetrahedron Lett., vol. 46, pp. 3201-3203 (2005).
Evans et al., Angew. Chem. vol. 48, pp. 6262-6265 (2009).
Wang et al., J. Org. Chem., vol. 76, pp. 3203-3221 (2011).

* cited by examiner

METHODS OF MAKING FUNCTIONALIZED INTERNAL OLEFINS AND USES THEREOF

CROSS-REFERENCE TO RELATED APPLICATIONS

The present application is a continuation application of U.S. patent application Ser. No. 14/090,762, filed Nov. 26, 2013, which claims the benefit of priority to U.S. Provisional Application No. 61/731,567, filed Nov. 30, 2012, both of which are hereby incorporated by reference as though fully set forth herein.

TECHNICAL FIELD

This disclosure relates generally methods of making functionalized internal olefins and the use of such compounds to make useful organic compounds. In some embodiments, the functionalized internal olefins are formed by isomerizing a functionalized terminal olefin to a functionalized internal olefin. In some embodiments, the functionalized internal olefins are derived from a renewable source, such as a natural oil or derivative thereof. In some such embodiments, the functionalized internal olefin is derived from the metathesis of a natural oil or a derivative thereof.

BACKGROUND

Renewable feedstocks, such as fatty acids or fatty esters derived from natural oils, have opened new possibilities for the development of industrially useful organic compounds. For example, renewable feedstocks can be used to prepare compounds that are not readily obtainable from conventional petroleum feedstocks. In another example, renewable feedstocks can be used to prepare known compounds more efficiently, without requiring undesirable reagents or solvents, and/or with decreased amounts of waste or side products.

Metathesis reactions can be used to convert natural oils and their fatty acid or fatty ester derivatives into useful renewable feedstocks. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical structures. Examples of useful unsaturated organic compounds that can be produced by metathesis reactions with natural oils or their derivatives include olefin ester compounds, e.g., terminal olefin esters such as "α-ester-alk-ω-ene molecules", for instance 9-decenoic acid methyl ester (9-DAME) and internal olefin esters, such as "α-ester-alk-ψ-ene molecules", for instance 9-dodecenoic acid methyl ester (9-DDAME).

Dibasic acids, such as dicarboxylic acids or their esters, are used to make a variety of different materials, including, but not limited to, polyamides, polyesters, and polyanhydrides. While some dicarboxylic acids can be readily synthesized from conventional petroleum-based feedstocks, others cannot. Suberic acid is one non-limiting example of an industrially useful organic compound that is difficult to prepare from conventional petroleum feedstocks. Suberic acid is one of a class of aliphatic, linear dicarboxylic acids having the chemical formula $HOOC-(CH_2)_n-COOH$, which are useful organic compounds having a variety of commercial applications. Some members of this class of dicarboxylic acids, such as adipic acid (n=4), azelaic acid (n=7), sebacic acid (n=8), and dodecanedioic acid (n=10), are produced commercially on relatively large scales. These dicarboxylic acids may be described as $C_6$, $C_9$, $C_{10}$ and $C_{12}$ dicarboxylic acids, respectively, where the subscript refers to the number of carbon atoms in the linear aliphatic chain, including the carbon atoms of the carboxylic acid groups. Suberic acid (n=6; $C_8$ dicarboxylic acid), however, is not readily produced on a large scale.

The lack of commercially available suberic acid can represent a gap in the toolbox of synthetic chemistry. The values of properties such as melting point, refractive index, and decarboxylation temperature alternate as the number of carbon atoms in the aliphatic, linear dicarboxylic acids changes between even numbers and odd numbers in the series of $C_2$ to $C_{12}$. For example, in species below $C_{12}$ the odd numbered dicarboxylic acids have lower melting points and higher solubilities in water than do the even numbered dicarboxylic acids before and after them in the series. These differences in properties of the dicarboxylic acids can result in macroscopic differences in the properties of polymers formed from monomers that include the acids. While adipic ($C_6$) and sebacic ($C_{10}$) acids are commonly used as monomers for polyamides, polyesters and polyurethanes, suberic acid ($C_8$) is not commonly used due to its relative lack of availability. Thus, polymers formed using suberic acid, which would have properties between those of polymers formed using adipic acid or sebacic acid, are not readily available.

It would be desirable to provide methods of making useful organic compounds, such as suberic acid, from renewable feedstocks. In one example, it would be desirable to provide methods of making other useful organic compounds from 9-decenoic acid methyl ester. In another example, it would be desirable to provide methods of making useful organic compounds such as suberic acid from renewable feedstocks, such as 9-decenoic acid methyl ester. Preferably the methods of making useful organic compounds from renewable feedstocks can be performed using smaller amounts of solvents and/or reagents relative to conventional processes, and/or can produce smaller amounts of undesirable side products.

SUMMARY

The scope of the present invention is defined solely by the appended claims, and is not affected to any degree by the statements within this summary.

In one aspect, a method of isomerizing a substance is provided that includes combining a substance including a terminal alkenyl group and a substance including a fluorosulfonic acid group in a reaction mixture, and forming a substance including a 2-alkenyl group from the substance including a terminal alkenyl group in the reaction mixture.

In another aspect, a method of functionalizing a substance is provided that includes combining a substance including a terminal alkenyl group and a substance including a fluorosulfonic acid group in a first reaction mixture, forming a substance including a 2-alkenyl group from the substance including a terminal alkenyl group in the first reaction mixture, combining the substance including the 2-alkenyl group and a functionalizing agent in a second reaction mixture, and forming a substance including a first functional group from the substance including the 2-alkenyl group in the second reaction mixture.

In another aspect, a method of making suberic acid is provided that includes combining 9-decenoic acid methyl ester and an acid in a first reaction mixture, forming 8-decenoic acid methyl ester from the 9-decenoic acid methyl ester in the first reaction mixture, combining the 8-decenoic acid methyl ester and an oxidizing agent in a second reaction mixture, and forming suberic acid from the 8-decenoic acid methyl ester in the second reaction mixture.

In a further aspect, a method of making a dicarboxylic acid is provided that includes forming a first reaction mixture from ingredients comprising a first olefin ester, a second olefin ester, and a metathesis catalyst; forming an unsaturated dicarboxylic ester from the first reaction mixture; forming a second reaction mixture from ingredients comprising the unsaturated dicarboxylic ester and a hydrogenating agent; forming a second dicarboxylic ester; forming a third reaction mixture from ingredients comprising the second dicarboxylic ester and a hydrolyzing agent; and hydrolyzing the second dicarboxylic ester, to form a dicarboxylic acid.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention. Moreover, in the figures, like referenced numerals designate corresponding parts throughout the different views.

DETAILED DESCRIPTION

Figure 1:
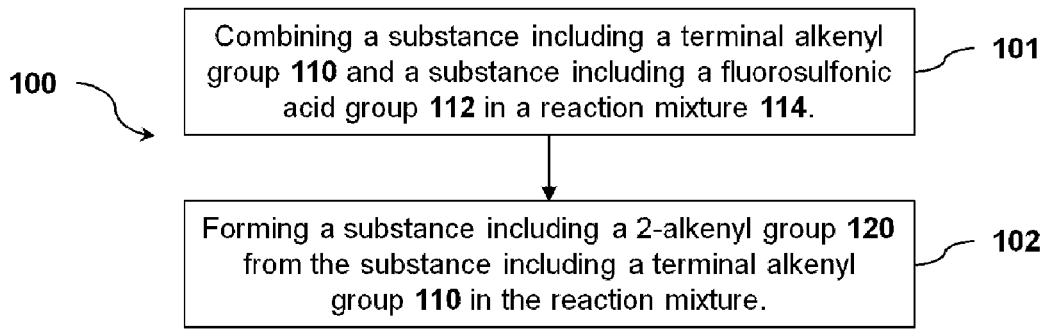
FIG. 1 represents a method of isomerizing a substance.

To provide a clear and more consistent understanding of the specification and claims of this application, the following definitions are provided.

The terms "reaction" and "chemical reaction" refer to the conversion of a substance into a product, irrespective of reagents or mechanisms involved.

The term "reaction product" refers to a substance produced from a chemical reaction of one or more reactant substances.

The term "yield" refers to the amount of reaction product formed in a reaction. When expressed with units of percent (%), the term yield refers to the amount of reaction product actually formed, as a percentage of the amount of reaction product that would be formed if all of the reactant were converted into the product.

The terms "isomerizing" and "isomerization" refer to a chemical reaction in which the atoms within a substance are retained, but are rearranged to have a different configuration.

The term "alkyl group" refers to a group formed by removing a hydrogen from a carbon of an alkane, where an alkane is an acyclic or cyclic compound consisting entirely of hydrogen atoms and saturated carbon atoms.

The term "alkenyl group" refers to a group formed by removing a hydrogen from a carbon of an alkene, where an alkene is an acyclic or cyclic compound consisting entirely of hydrogen atoms and carbon atoms, and including at least one carbon-carbon double bond.

The term "terminal alkenyl group" refers to an alkenyl group that is positioned at the end of a chain of at least 4 carbon atoms.

The term "allyl alkenyl group" refers to an alkenyl group that is positioned at the penultimate position of a chain of at least 4 carbon atoms.

The term "unsaturated group" refers to a group that includes a carbon-carbon double bond or a carbon-carbon triple bond.

The term "fluorosulfonic acid group" refers to a group having the formula $R—CF_xH_{2-x}SO_3H$, where R is a fluorine atom or an organic group. If R is a fluorine atom, then x is 0, 1 or 2. If R is an organic group, then x is 1 or 2.

The term "functional group" refers to a group that includes one or a plurality of atoms other than hydrogen and $sp^3$ carbon atoms. Examples of functional groups include but are not limited to hydroxyl (—OH), protected hydroxyl, ether (—C—O—C—), ketone (—C(=O)—), ester (—C(=O)O—C—), carboxylic acid (—C(=O)OH), cyano (—C≡N), amido (—C(=O)NH—C—), isocyanate (—N=C=O), urethane (—O—C(=O)—NH—), urea (—NH—C(=O)—NH—), protected amino, thiol (—SH), sulfone, sulfoxide, phosphine, phosphite, phosphate, halide (—X), and the like.

The term "functionalizing agent" refers to a reactant that is combined with a substance to convert the substance into a product having at least one new functional group not present in the substance.

The term "oxidizing agent" refers to a functionalizing agent that is combined with a substance to convert at least one group in the substance into a new functional group having a higher oxidation state.

The term "hydrogenating agent" refers to an agent that is combined with a substance to hydrogenate at least one unsaturated group in the substance.

The term "hydrolyzing agent" refers to a functionalizing agent that is combined with a substance to convert at least one ester group in the substance to a carboxylic acid group or one of its salts.

The term "substituent" refers to a group that replaces one or more hydrogen atoms in a molecular entity. Examples of substituents include but are not limited to halide groups, alkyl groups, heteroalkyl groups, aryl groups, and heteroaryl groups. A heteroalkyl or heteroaryl substituent may be bonded to the remainder of the molecular entity through a carbon or through a heteroatom.

The term "metathesis catalyst" refers to any catalyst or catalyst system configured to catalyze a metathesis reaction.

The terms "metathesize" and "metathesizing" refer to a chemical reaction involving a single type of olefin or a plurality of different types of olefin, which is conducted in the presence of a metathesis catalyst, and which results in the formation of at least one new olefin product. The phrase "metathesis reaction" encompasses cross-metathesis (a.k.a. co-metathesis), self-metathesis, ring-opening metathesis (ROM), ring-opening metathesis polymerizations (ROMP), ring-closing metathesis (RCM), and acyclic diene metathesis (ADMET), and the like, and combinations thereof.

The terms "natural oils", "natural feedstocks", or "natural oil feedstocks" mean oils derived from plants or animal sources. Examples of natural oils include but are not limited to vegetable oils, algal oils, animal fats, tall oils, derivatives of these oils, combinations of any of these oils, and the like. Examples of vegetable oils include but are not limited to canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, camelina oil, pennycress oil, castor oil, and the like, and combinations thereof. Examples of animal fats include but are not limited to lard, tallow, poultry fat, yellow grease, fish oil, and the like, and combinations thereof. Tall oils are by-products of wood pulp manufacture. A natural oil may be refined, bleached, and/or deodorized.

The term "natural oil derivatives" refers to compounds or mixtures of compounds derived from one or more natural oils using any one or combination of methods known in the art. Such methods include but are not limited to saponification, transesterification, esterification, hydrogenation (partial or full), isomerization, oxidation, reduction, and the like, and combinations thereof. Examples of natural oil derivatives include but are not limited to gums, phospholipids, soapstock, acidulated soapstock, distillate or distillate sludge, fatty acids and fatty acid alkyl ester such as 2-ethylhexyl ester, hydroxy-substituted variations thereof of the natural oil, and the like, and combinations thereof. For example, the natural oil derivative may be a fatty acid methyl ester (FAME) derived from the glyceride of the natural oil.

The term "metathesized natural oil" refers to the metathesis reaction product of a natural oil in the presence of a metathesis catalyst, where the metathesis product includes a new olefinic compound. A metathesized natural oil may include a reaction product of two triglycerides in a natural feedstock (self-metathesis) in the presence of a metathesis catalyst, where each triglyceride has an unsaturated carbon-carbon double bond, and where the reaction product includes a "natural oil oligomer" having a new mixture of olefins and esters that may include one or more of metathesis monomers, metathesis dimers, metathesis trimers, metathesis tetramers, metathesis pentamers, and higher order metathesis oligomers (e.g., metathesis hexamers). A metathesized natural oil may include a reaction product of a natural oil that includes more than one source of natural oil (e.g., a mixture of soybean oil and palm oil). A metathesized natural oil may include a reaction product of a natural oil that includes a mixture of natural oils and natural oil derivatives.

The term "dicarboxylic acid" refers to a compound featuring at least two carboxylic acid functional groups, or their salts. Non-limiting examples of dicarboxylic acids include aliphatic, linear dicarboxylic acids having the chemical formula $HOOC-(CH_2)_n-COOH$, where n is a positive integer number. Other representative examples of dicarboxylic acids feature other types of carbon chains, e.g. linear olefinic, branched aliphatic, and branched olefinic. In additional representative examples, the carboxylic acid functional groups may be appended to cycloalkyl, cycloalkenyl, or aromatic moieties.

The term "catalyst poison" includes any chemical species or impurity in a reaction mixture that reduces or is capable of reducing the functionality (e.g., efficiency, conversion, turnover number) of a metathesis catalyst. The term "turnover number" or "catalyst turnover" generally refers to the number of moles of feedstock that a mole of catalyst can convert before becoming deactivated.

The terms "hydrogenation" and "hydrogenating", refer to processes where one or more unsaturated groups in a molecule are hydrogenated. For example, a carbon-carbon double bond may be hydrogenated to a single bond between two $sp^3$ carbon atoms, while a carbon-carbon triple bond may be hydrogenated to a carbon-carbon double bond or to a single bond between two $sp^3$ carbon atoms.

The terms "selective hydrogenation", or "partial hydrogenation" refers to a hydrogenation process which converts an unsaturated molecule such as an alkyne or a diolefin to a less unsaturated molecule, such as a mono-olefin, without hydrogenating the less unsaturated molecule to a saturated or a more saturated hydrocarbon, such as an alkane.

A method of isomerizing a substance includes combining a substance including a terminal alkenyl group and a substance including a fluorosulfonic acid group in a reaction mixture, and forming a substance including a 2-alkenyl group from the substance including a terminal alkenyl group in the reaction mixture. The substance including a 2-alkenyl group may be functionalized, such as by reacting the 2-alkenyl group with a functionalizing agent, to form a substance including a first functional group. In one example, the isomerization and subsequent functionalization may be used to form suberic acid from 9-decenoic acid methyl ester (9-DAME).

Isomerizing a substance containing a terminal alkenyl group can facilitate the production of useful organic compounds from renewable feedstocks. As renewable feedstocks may include substances having terminal alkenyl groups, selective isomerization of these substances can provide substances having a 2-alkenyl group instead of a terminal alkenyl group. Substances that differ only in the position of an alkenyl group may have distinct chemical and/or physical properties. In one example, the product of a reaction between a functionalizing agent and a substance having a 2-alkenyl group may have different chemical and/or physical properties from the product of a reaction between the functionalizing agent and the original substance having the terminal alkenyl group.

Producing organic compounds from renewable feedstocks may provide new compounds that have not been produced previously. Producing organic compounds from renewable feedstocks also may provide certain advantages over existing production methods, including but not limited to simpler and/or more cost-effective production, reduced variability, improved sourcing, and increased biorenewability.

FIG. 1 represents a method 100 of isomerizing a substance. The method 100 includes combining 101 a substance including a terminal alkenyl group 110 and a substance including a fluorosulfonic acid group 112 in a reaction mixture 114; and forming 102 a substance including a 2-alkenyl group 120 from the substance including a terminal alkenyl group 110 in the reaction mixture.

The substance including a terminal alkenyl group 110 may include any organic molecule that includes a chain of at least 4 carbon atoms and an alkenyl group positioned at the end of the chain. Examples of substances including a terminal alkenyl group include but are not limited to unsaturated hydrocarbons, such as 1-butene, 1-pentene, 1-hexene, 1-heptene, 1-octene, 1-nonene, and 1-decene. Examples of substances including a terminal alkenyl group include but are not limited to substituted unsaturated hydrocarbons that include a substituent in place of a hydrogen atom. Examples of substituents include but are not limited to halide groups, heteroalkyl groups, aryl groups, heteroaryl groups, nitrile groups, amide groups, imide groups, nitro groups, ketone groups, ether groups, sulfide groups, sulfoxide groups and sulfone groups.

The substance including a terminal alkenyl group 110 may include an α-ester-alk-ω-ene molecule. An α-ester-alk-ω-ene molecule has the chemical formula R—O—C(=O)—(R$^1$)—CH=CH$_2$, where R is a alkyl group having from 1 to 5 carbon atoms, and R$^1$ is an alkyl group having from 2 to 20 carbon atoms. Examples of α-ester-alk-ω-ene molecules include but are not limited to 9-decenoic acid methyl ester, 9-decenoic acid ethyl ester, 9-decenoic acid propyl ester, 10-undecenoic acid methyl ester, 10-undecenoic acid ethyl ester, 10-decenoic acid propyl ester, 11-dodecenoic acid methyl ester, 11-dodecenoic acid ethyl ester, and 11-dodecenoic acid propyl ester.

The substance including a terminal alkenyl group 110 may include a terminal alkenyl group 110 that is the product of a metathesis reaction of a natural oil in the presence of a metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in paragraphs [0069]-[0155] of US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst comprises a transition metal. In some embodiments, the metathesis catalyst comprises ruthenium. In some embodiments, the metathesis catalyst comprises rhenium. In some embodiments, the metathesis catalyst comprises tantalum. In some embodiments, the metathesis catalyst comprises nickel. In some embodiments, the metathesis catalyst comprises tungsten. In some embodiments, the metathesis catalyst comprises molybdenum.

In some embodiments, the metathesis catalyst comprises a ruthenium carbene complex and/or an entity derived from such a complex. In some embodiments, the metathesis catalyst comprises a material selected from the group consisting of a ruthenium vinylidene complex, a ruthenium alkylidene complex, a ruthenium methylidene complex, a ruthenium benzylidene complex, and combinations thereof, and/or an entity derived from any such complex or combination of such complexes. In some embodiments, the metathesis catalyst comprises a ruthenium carbene complex comprising at least one phosphine ligand and/or an entity derived from such a complex. In some embodiments, the metathesis catalyst comprises a ruthenium carbene complex comprising at least one tricyclohexylphosphine ligand and/or an entity derived from such a complex. In some embodiments, the metathesis catalyst comprises a ruthenium carbene complex comprising at least two tricyclohexylphosphine ligands [e.g., (PCy$_3$)$_2$Cl$_2$Ru=CH—CH=C(CH$_3$)$_2$, etc.] and/or an entity derived from such a complex. In some embodiments, the metathesis catalyst comprises a ruthenium carbene complex comprising at least one imidazolidine ligand and/or an entity derived from such a complex. In some embodiments, the metathesis catalyst comprises a ruthenium carbene complex comprising an isopropyloxy group attached to a benzene ring and/or an entity derived from such a complex.

In some embodiments, the metathesis catalyst comprises a Grubbs-type olefin metathesis catalyst and/or an entity derived therefrom. In some embodiments, the metathesis catalyst comprises a first-generation Grubbs-type olefin metathesis catalyst and/or an entity derived therefrom. In some embodiments, the metathesis catalyst comprises a second-generation Grubbs-type olefin metathesis catalyst and/or an entity derived therefrom. In some embodiments, the metathesis catalyst comprises a first-generation Hoveyda-Grubbs-type olefin metathesis catalyst and/or an entity derived therefrom. In some embodiments, the metathesis catalyst comprises a second-generation Hoveyda-Grubbs-type olefin metathesis catalyst and/or an entity derived therefrom. In some embodiments, the metathesis catalyst comprises one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst comprises a molybdenum and/or tungsten carbene complex and/or an entity derived from such a complex. In some embodiments, the metathesis catalyst comprises a Schrock-type olefin metathesis catalyst and/or an entity derived therefrom. In some embodiments, the metathesis catalyst comprises a high-oxidation-state alkylidene complex of molybdenum and/or an entity derived therefrom. In some embodiments, the metathesis catalyst comprises a high-oxidation-state alkylidene complex of tungsten and/or an entity derived therefrom. In some embodiments, the metathesis catalyst comprises molybdenum (VI). In some embodiments, the metathesis catalyst comprises tungsten (VI). In some embodiments, the metathesis catalyst comprises a molybdenum- and/or a tungsten-containing alkylidene complex of a type described in one or more of (a) *Angew. Chem. Int. Ed. Engl.*, 2003, 42, 4592-4633; (b) *Chem. Rev.*, 2002, 102, 145-179; and/or (c) *Chem. Rev.*, 2009, 109, 3211-3226, each of which is incorporated by reference herein in its entirety, except that in the event of any inconsistent disclosure or definition from the present specification, the disclosure or definition herein shall be deemed to prevail.

Metathesis is a catalytic reaction that involves the interchange of alkylidene units among compounds containing one or more double bonds (i.e., olefinic compounds) via the formation and cleavage of the carbon-carbon double bonds. The substance including a terminal alkenyl group 110 may be formed by a metathesis reaction of a natural oil containing unsaturated polyol esters, including a cross-metathesis reaction of a natural oil with an alpha-olefin or with ethylene. The substance including a terminal alkenyl group 110 may be formed by a metathesis reaction of a metathesized natural oil containing unsaturated polyol esters, including a cross-metathesis reaction of a metathesized natural oil with an alpha-olefin or with ethylene. Examples of cross-metathesis reactions of natural oils and/or of metathesized natural oils that can produce substances including terminal alkenyl groups are described in US 2010/0145086 and in US 2012/0071676, which are incorporated by reference herein in their entirety, except that in the event of any inconsistent disclosure or definition from the present specification, the disclosure or definition herein shall be deemed to prevail.

Examples of natural oils include but are not limited to vegetable oil, algal oil, animal fat, tall oil, derivatives of these oils, or mixtures thereof. Examples of vegetable oils include but are not limited to canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, camelina oil, pennycress oil, castor oil, and the like, and combinations thereof. Examples of animal fats include but are not limited to lard, tallow, poultry fat, yellow grease, fish oil, and the like, and combinations thereof. Examples of natural oil derivatives include but are not limited to metathesis oligomers, gums, phospholipids, soapstock, acidulated soapstock, distillate or distillate sludge, fatty acids and fatty acid alkyl ester such as 2-ethylhexyl ester, hydroxyl-substituted variations of the natural oil, and the like, and combinations thereof. For example, the natural oil derivative may be a fatty acid methyl ester (FAME) derived from the glyceride of the natural oil.

The natural oil may include canola or soybean oil, such as refined, bleached and deodorized soybean oil (i.e., RBD soybean oil). Soybean oil typically includes 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

The substance including a terminal alkenyl group 110 may be formed by a cross-metathesis reaction of a natural oil and/or a metathesized natural oil containing unsaturated polyol esters with an alpha-olefin or with ethylene. An alpha-olefin is a hydrocarbon having an alkene group, where a first carbon of the alkene group is unsubstituted and a second carbon of the alkene group is substituted with one or two non-hydrogen substituents. The alpha-olefin may include from 3 to 20 carbon atoms, 10 carbon atoms, 6 carbon atoms, or 3 carbon atoms. A cross-metathesis reaction may involve a single species of alpha-olefin, or it may involve a mixture of alpha-olefin species.

As an example, an alpha-olefin for use in cross-metathesis may have the structure $H_2C=C(R^2)(R^3)$, where $R^2$ and $R^3$ are independently hydrogen, a hydrocarbyl group, or a heteroalkyl group, provided that at least one of $R^2$ and $R^3$ is not hydrogen. The heteroatoms of a heteroalkyl group may be present as part of a functional group substituent. $R^2$ and $R^3$ may be linked to form a cyclic structure. In a preferred embodiment, $R^2$ and $R^3$ are independently selected from $C_1$-$C_{20}$ alkyl, $C_2$-$C_{20}$ alkenyl, $C_2$-$C_{20}$ alkynyl, $C_1$-$C_{20}$ heteroalkyl, $C_2$-$C_{20}$ heteroalkenyl, $C_2$-$C_{20}$ heteroalkynyl, $C_5$-$C_{24}$ aryl, $C_6$-$C_{24}$ alkylaryl, $C_6$-$C_{24}$ arylalkyl, $C_5$-$C_{24}$ heteroaryl, and $C_6$-$C_{24}$ heteroarylalkyl.

Examples of monosubstituted alpha-olefins that may be used in cross-metathesis include 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene and larger alpha olefins, 2-propenol, 3-butenol, 4-pentenol, 5-hexenol, 6-heptenol, 7-octenol, 8-nonenol, 9-decenol, 10-undecenol, 11-dodecenol, 12-tridecenol, 13-tetradecenol, 14-pentadecenol, 15-hexadecenol, 16-heptadecenol, 17-octadecenol, 18-nonadecenol, 19-eicosenol and larger alpha alkenols, 2-propenyl acetate, 3-butenyl acetate, 4-pentenyl acetate, 5-hexenyl acetate, 6-heptenyl acetate, 7-octenyl acetate, 8-nonenyl acetate, 9-decenyl acetate, 10-undecenyl acetate, 11-dodecenyl acetate, 12-tridecenyl acetate 13-tetradecenyl acetate, 14-pentadecenyl acetate, 15-hexadecenyl acetate, 16-heptadecenyl acetate, 17-octadecenyl acetate, 18-nonadecenyl acetate, 19-eicosenyl acetate and larger alpha-alkenyl acetates, 2-propenyl chloride, 3-butenyl chloride, 4-pentenyl chloride, 5-hexenyl chloride, 6-heptenyl chloride, 7-octenyl chloride, 8-nonenyl chloride, 9-decenyl chloride, 10-undecenyl chloride, 11-dodecenyl chloride, 12-tridecenyl chloride, 13-tetradecenyl chloride, 14-pentadecenyl chloride, 15-hexadecenyl chloride, 16-heptadecenyl chloride, 17-octadecenyl chloride, 18-nonadecenyl chloride, 19-eicosenyl chloride and larger alpha-alkenyl chlorides, bromides, and iodides, allyl cyclohexane, allyl cyclopentane, and the like. Examples of disubstituted alpha-olefins that may be used in cross-metathesis include isobutylene, 2-methylbut-1-ene, 2-methylpent-1-ene, 2-methylhex-1-ene, 2-methylhept-1-ene, 2-methyloct-1-ene, and the like.

Any combination of any of these alpha-olefins may be used in a cross-metathesis reaction with a natural oil and/or a metathesized natural oil containing unsaturated polyol esters, to provide the substance including a terminal alkenyl group 110. In an exemplary embodiment, a composition including 9-DAME, which includes a terminal alkenyl group, can be prepared by the cross-metathesis of 1-propene with a natural oil and/or a metathesized natural oil containing unsaturated polyol esters. For example, oleic acid and/or methyl oleate may undergo cross-metathesis with 1-propene to provide a composition including 9-DAME. Due to the stoichiometry of the cross-metathesis reaction, the product composition typically comprises 50 mole percent (mol %) 9-DAME and 50 mol % 9-undecenoic acid methyl ester.

Ethylene also may be used in a cross-metathesis reaction with a natural oil and/or a metathesized natural oil containing unsaturated polyol esters, to provide the substance including a terminal alkenyl group 110. In an exemplary embodiment, a composition including 9-DAME, which includes a terminal alkenyl group, can be prepared by the cross-metathesis of ethylene with a natural oil and/or a metathesized natural oil containing unsaturated polyol esters. For example, methyl oleate may undergo cross-metathesis with ethylene to provide a composition including 9-DAME. Due to the stoichiometry of the cross-metathesis reaction, the product composition typically comprises 50 mol % 9-DAME and 50 mol % 1-decene.

The substance including a fluorosulfonic acid group 112 includes a group having the formula $R^4\text{—}CF_xH_{2-x}SO_3H$, where R is a fluorine atom or an organic group. In one example $R^4$ is a fluorine atom, and x is 0, 1 or 2. In this example, the substance including the fluorosulfonic acid group is fluoromethanesulfonic acid, difluoromethanesulfonic acid, or trifluoromethanesulfonic acid. In another example $R^4$ is an organic group, and x is 1 or 2. In this example, the substance including the fluorosulfonic acid group may be a partially fluorinated alkyl sulfonic acid such as tetrafluoroethanesulfonic acid, or a perfluorinated alkyl sulfonic acid such as pentafluoroethanesulfonic acid.

In another example, the substance including a fluorosulfonic acid group may be a material having a surface that includes fluorosulfonic acid groups attached to the surface. Examples of materials having a surface that includes fluorosulfonic acid groups attached to the surface include copolymers having perfluorosulfonic acid monomeric units and monomer units derived from tetrafluoroethylene, such as a NAFION copolymer (DuPont, Wilmington, Del.). In one example, a NAFION copolymer may be in the form of a dispersion of copolymer particles in a liquid, or in the form of a dispersion of particles having a coating of copolymer on the particles.

The reaction mixture 114 includes the substance including a terminal alkenyl group 110 and the substance including a fluorosulfonic acid group 112. The reaction mixture may include only these two substances, or it may include one or more other substances, such as a solvent, a buffer or a salt. Examples of solvents include but are not limited to protic solvents such as water, methanol, ethanol, isopropyl alcohol (IPA) and butanol, and include aprotic solvents such as tetrahydrofuran (THF), dioxane, dimethyl formamide (DMF), toluene and xylene.

The forming 102 of a substance including a 2-alkenyl group 120 from the substance including a terminal alkenyl group 110 in the reaction mixture may include heating the reaction mixture. The reaction mixture may be heated to a temperature of at least 30° C., including but not limited to a temperature from 30° C. to 200° C., from 40° C. to 175° C., from 50° C. to 150° C., or from 60° C. to 120° C. The reaction mixture may be heated for at least 1 hour, including but not limited to from 1 hour to 100 hours, from 5 hours to 50 hours, from 10 hours to 30 hours, or from 15 hours to 25 hours.

The substance including a 2-alkenyl group 120 may include any organic molecule that includes a chain of at least 4 carbon atoms and an alkenyl group positioned at the penultimate position of the chain. Examples of substances including a 2-alkenyl group include but are not limited to unsaturated hydrocarbons, such as 2-butene, 2-pentene, 2-hexene, 2-heptene, 2-octene, 2-nonene, and 2-decene. Examples of substances including a 2-alkenyl group include but are not limited to substituted unsaturated hydrocarbons that include a substituent in place of a hydrogen atom. Examples of substituents include but are not limited to halide groups, alkyl groups, heteroalkyl groups, aryl groups, heteroaryl groups, nitrile groups, amide groups, imide groups, nitro groups, ketone groups, ether groups, sulfide groups, sulfoxide groups and sulfone groups.

The substance including a 2-alkenyl group 120 may include an α-ester-alk-ψ-ene molecule. An α-ester-alk-ψ-ene molecule has the chemical formula $R^5\text{—}O\text{—}C(=O)\text{—}(R^6)\text{—}CH=CH\text{—}CH_3$, where $R^5$ is a alkyl group having from 1 to 5 carbon atoms, and $R^6$ is an alkyl group having from 1 to 19 carbon atoms. Examples of α-ester-alk-ψ-ene molecules include 8-decenoic acid methyl ester, 8-decenoic acid ethyl ester, 8-decenoic acid propyl ester, 9-undecenoic acid methyl ester, 9-undecenoic acid ethyl ester, 9-decenoic acid propyl ester, 10-dodecenoic acid methyl ester, 10-dodecenoic acid ethyl ester, and 10-dodecenoic acid propyl ester.

The yield of the substance comprising a 2-alkenyl group 120 may be at least 50%. Preferably the yield of the substance comprising a 2-alkenyl group 120 is at least 60%, at least 70%, at least 80%, at least 90%, or at least 95%.

Method 100 may produce a substance containing a 2-alkenyl group 120 from renewable feedstocks, and may advantageously provide simpler and/or more cost-effective production, reduced variability, improved sourcing, and increased biorenewability than conventional methods for producing substances containing a 2-alkenyl group from petrochemical feedstocks. In addition, method 100 may have less environmental impact than conventional isomerization methods, which typically utilize organic solvents and transition metal catalysts such as iron, nickel or palladium complexes.

Figure 2:
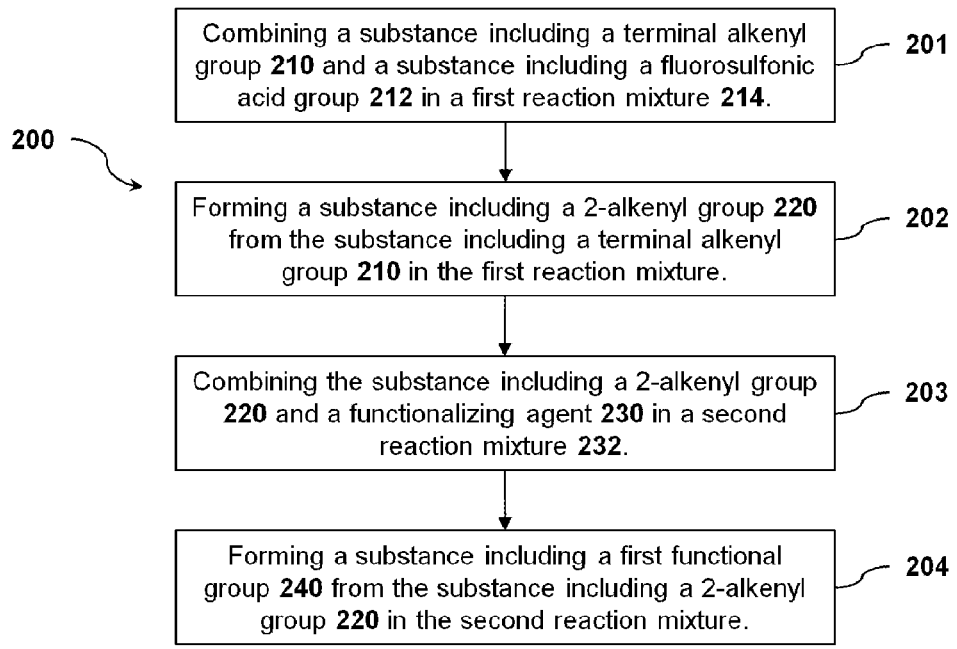
FIG. 2 represents a method of functionalizing a substance.

FIG. 2 represents a method 200 of functionalizing a substance. The method 200 includes combining 201 a substance including a terminal alkenyl group 210 and a substance including a fluorosulfonic acid group 212 in a first reaction mixture 214, forming 202 a substance including a 2-alkenyl group 220 from the substance including a terminal alkenyl group 210 in the first reaction mixture, combining 203 the substance including a 2-alkenyl group 220 and a functionalizing agent 230 in a second reaction mixture 232, and forming 204 a substance including a first functional group 240 from the substance including a 2-alkenyl group 220 in the second reaction mixture.

The substance including a terminal alkenyl group 210, the substance including a fluorosulfonic acid group 212, and the substance including a 2-alkenyl group 220 may be as described above for the substances including a terminal alkenyl group 110, a fluorosulfonic acid group 112 or a 2-alkenyl group 120, respectively. The first reaction mixture 214 and the forming 202 of a substance including a 2-alkenyl group 220 from the substance including a terminal alkenyl group 210 in the first reaction mixture may be as described above for the reaction mixture 114 and the forming 102, respectively.

The functionalizing agent 230 may include any reagent known to convert a carbon-carbon double bond into another functional group. The functionalizing agent 230 may include a halogen, such as $Cl_2$ or $Br_2$, which can react with the substance including a 2-alkenyl group 220 to form a 1,2-dihalide functional group or a 1,2-halohydrin functional group. The functionalizing agent 230 may include hydrobromic acid (HBr), which can react with the substance including a 2-alkenyl group 220 to form a halide functional group. The functionalizing agent 230 may include an aqueous acid, such as sulfuric acid, which can react with the substance including a 2-alkenyl group 220 to form an alcohol functional group. The functionalizing agent 230 may include oxymercuration reagents, such as water, mercuric acetate ($Hg(OAc)_2$) and sodium borohydride ($NaBH_4$), which can react with the substance including a 2-alkenyl group 220 to form an alcohol functional group. The functionalizing agent 230 may include hydroxylation reagents, such as potassium permanganate ($KMnO_4$) or osmium tetraoxide ($OsO_4$), which can react with the substance including a 2-alkenyl group 220 to form a 1,2-diol functional group.

The functionalizing agent 230 may include epoxidation reagents, such as peracetic acid, which can react with the substance including a 2-alkenyl group 220 to form an epoxide functional group. The functionalizing agent 230 may include alkoxymercuration reagents, such as an alcohol, mercuric acetate or mercuric trifluoroacetate (Hg(OOCCF$_3$)$_2$) and sodium borohydride (NaBH$_4$), which can react with the substance including a 2-alkenyl group 220 to form an ether functional group. The functionalizing agent 230 may include maleination reagents, such as maleic anhydride, which can react with the substance including a 2-alkenyl group 220 to form an maleinate functional group. The functionalizing agent 230 may include hydroamination reagents, such as a primary or secondary amine and a rhodium catalyst, which can react with the substance including a 2-alkenyl group 220 to form an amine functional group. The functionalizing agent 230 may include borane (BH$_3$), which can react with the substance including a 2-alkenyl group 220 to form an alkyl borane functional group. The functionalizing agent 230 may include dimethyl disulfide and iodine (I$_2$), which can react with the substance including a 2-alkenyl group 220 to form a α,β-bis-methylthioether functional group. The functionalizing agent 230 may include a metathesis catalyst and another alkene that includes a functional group, which can react with the substance including a 2-alkenyl group 220 to form a metathesized product that includes the functional group originally present in the alkene.

In one example, the functionalizing agent 230 includes an oxidizing agent. Examples of oxidizing agents include KMnO$_4$, ozone, periodic acid, and lead tetraacetate. An oxidizing agent can react with the substance including a 2-alkenyl group 220 to form a carboxylic acid group. A carboxylic acid group may be formed by a single reaction, such as the oxidation of the alkenyl group by ozone or KMnO$_4$. A carboxylic acid group may be formed by two or more reactions, such as the formation of a 1,2-diol functional group, followed by oxidative cleavage of the 1,2-diol group with periodic acid or lead tetraacetate.

The second reaction mixture 232 includes the substance including a 2-alkenyl group 220 and the functionalizing agent 230. The second reaction mixture may be limited to include essentially these two substances, or it may include one or more other substances, such as a solvent, a buffer or a salt. Examples of solvents include but are not limited to protic solvents such as water, methanol, ethanol, isopropyl alcohol (IPA) and butanol, and include aprotic solvents such as tetrahydrofuran (THF), dioxane, dimethyl formamide (DMF), toluene and xylene.

The forming 204 of a substance including a first functional group 240 from the substance including a 2-alkenyl group 220 in the second reaction mixture may include heating the reaction mixture. The reaction mixture may be heated to a temperature of at least 30° C., including but not limited to a temperature from 30° C. to 200° C., from 40° C. to 175° C., from 50° C. to 150° C., or from 60° C. to 120° C. The reaction mixture may be heated for at least 1 hour, including but not limited to from 1 hour to 100 hours, from 5 hours to 50 hours, from 10 hours to 30 hours, or from 15 hours to 25 hours.

The substance including a first functional group 240 may include an alkyl ester or alkyl carboxylic acid group, as a second functional group, in addition to the first functional group. Examples of alkyl ester groups include but are not limited to a methylheptanoate group, an ethylheptanoate group, a propylheptanoate group, a methyloctanoate group, an ethyloctanoate group, a propyloctanoate group, a methylnonanoate group, an ethylnonanoate group, and a propylnonanoate group. Examples of alkyl carboxylic acid groups include but are not limited to a heptanoic acid group, an octanoic acid group, a nonanoic acid group, and salts thereof.

The substance including a first functional group 240 may include two carboxylic acid groups. In one example, the substance including a 2-alkenyl group 220 includes an α-ester-alk-ψ-ene molecule, such as a molecule as described above for the substance including a 2-alkenyl group 120. Oxidation of the alkenyl group and in situ ester hydrolysis can provide a dicarboxylic acid molecule. Examples of dicarboxylic acid molecules that can be formed in this manner include but are not limited to suberic acid, azelaic acid, and sebacic acid.

Figure 3:
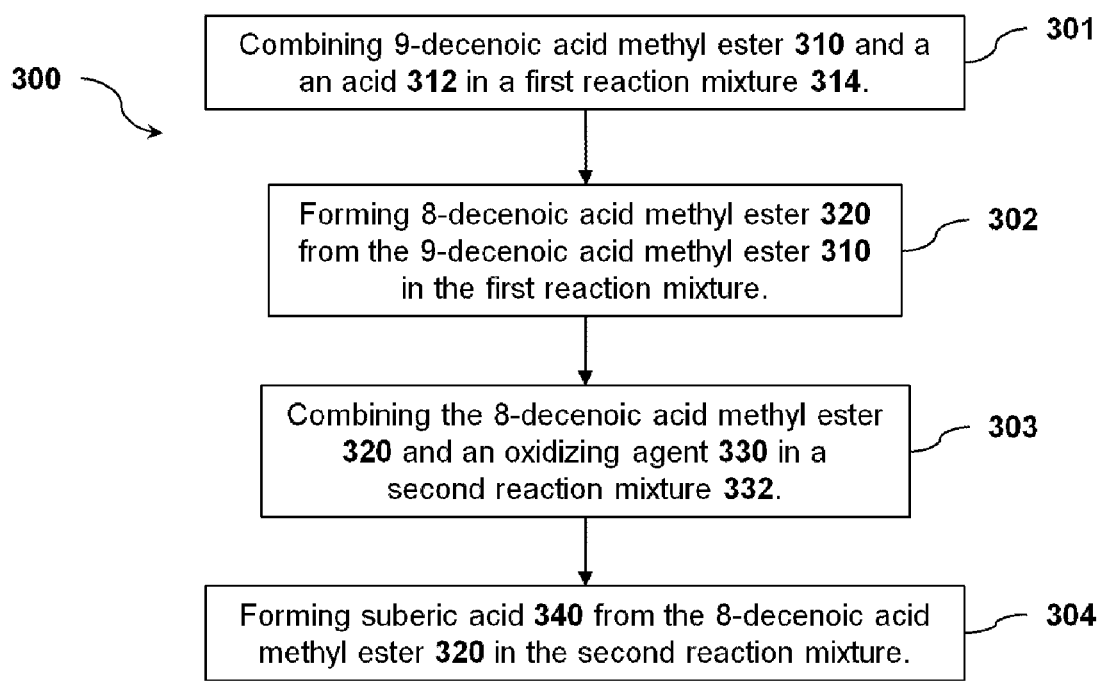
FIG. 3 represents a method of making suberic acid.

FIG. 3 represents a method 300 of making suberic acid. The method 300 includes combining 301 9-decenoic acid methyl ester 310 and an acid 312 in a first reaction mixture 314, forming 302 8-decenoic acid methyl ester 320 from the 9-decenoic acid methyl ester 310 in the first reaction mixture, combining 303 the 8-decenoic acid methyl ester 320 and an oxidizing agent 330 in a second reaction mixture 332, and forming 304 suberic acid 340 from the 8-decenoic acid methyl ester 320 in the second reaction mixture.

The 9-decenoic acid methyl ester 310 may be formed by metathesis, as described above for the substance including a terminal alkenyl group 110. Specifically, the 9-decenoic acid methyl ester 310 may be formed by a cross-metathesis reaction of a natural oil and/or a metathesized natural oil containing unsaturated polyol esters with an alpha-olefin or with ethylene. In an exemplary embodiment, a composition including 9-DAME 310 can be prepared by the cross-metathesis of 1-propene with a natural oil and/or a metathesized natural oil containing unsaturated polyol esters, such as oleic acid or methyl oleate. In another exemplary embodiment, a composition including 9-DAME 310 can be prepared by the cross-metathesis of ethylene with a natural oil and/or a metathesized natural oil such as methyl oleate.

The acid 312 may include a substance including a fluorosulfonic acid group, as described above for the substance including a fluorosulfonic acid group 112. For example, the acid 312 may include fluoromethanesulfonic acid, difluoromethanesulfonic acid, trifluoromethanesulfonic acid, a partially fluorinated alkyl sulfonic acid such as tetrafluoroethanesulfonic acid, and/or a perfluorinated alkyl sulfonic acid such as pentafluoroethanesulfonic acid. In another example, the acid 312 may be a material having a surface that includes fluorosulfonic acid groups attached to the surface, such as copolymers having perfluorosulfonic acid monomeric units and monomer units derived from tetrafluoroethylene, such as a NAFION copolymer (DuPont, Wilmington, Del.).

The first reaction mixture 314 includes the 9-decenoic acid methyl ester 310 and the acid 312. The first reaction mixture may include only these two substances, or it may include one or more other substances, such as a solvent, a buffer or a salt. Examples of solvents include but are not limited to protic solvents such as water, methanol, ethanol, isopropyl alcohol (IPA) and butanol, and include aprotic solvents such as tetrahydrofuran (THF), dioxane, dimethyl formamide (DMF), toluene and xylene.

The forming 302 of 8-decenoic acid methyl ester 320 may include heating the reaction mixture. The reaction mixture may be heated to a temperature of at least 30° C., including but not limited to a temperature from 30° C. to 200° C., from 40° C. to 175° C., from 50° C. to 150° C., or from 60° C. to 120° C. The reaction mixture may be heated for at least 1 hour, including but not limited to from 1 hour to 100 hours, from 5 hours to 50 hours, from 10 hours to 30 hours, or from 15 hours to 25 hours.

The oxidizing agent 330 may be as described above for the functionalizing agent 230, when the functionalizing agent includes an oxidizing agent. Examples of oxidizing agents include $KMnO_4$, ozone, hydrogen peroxide, peroxy acids, periodic acid, and lead tetraacetate. An oxidizing agent can react with 8-decenoic acid methyl ester 320 to form a carboxylic acid group. A carboxylic acid group may be formed by a single reaction, such as the oxidation of the alkenyl group by ozone or $KMnO_4$. A carboxylic acid group may be formed by two or more reactions, such as the formation of a 1,2-diol functional group, followed by oxidative cleavage of the 1,2-diol group with periodic acid or lead tetraacetate.

The second reaction mixture 332 includes the 8-decenoic acid methyl ester 320 and the oxidizing agent 330. The second reaction mixture may include only these two substances, or it may include one or more other substances, such as a solvent, a buffer or a salt. Examples of solvents include but are not limited to protic solvents such as water, methanol, ethanol, isopropyl alcohol (IPA) and butanol, and include aprotic solvents such as tetrahydrofuran (THF), dioxane, dimethyl formamide (DMF), toluene and xylene.

The forming 304 of suberic acid 340 from the 8-decenoic acid methyl ester 320 may include heating the second reaction mixture. The second reaction mixture may be heated to a temperature of at least 30° C., including but not limited to a temperature from 30° C. to 200° C., from 40° C. to 175° C., from 50° C. to 150° C., or from 60° C. to 120° C. The second reaction mixture may be heated for at least 1 hour, including but not limited to from 1 hour to 100 hours, from 5 hours to 50 hours, from 10 hours to 30 hours, or from 15 hours to 25 hours.

Figure 4:
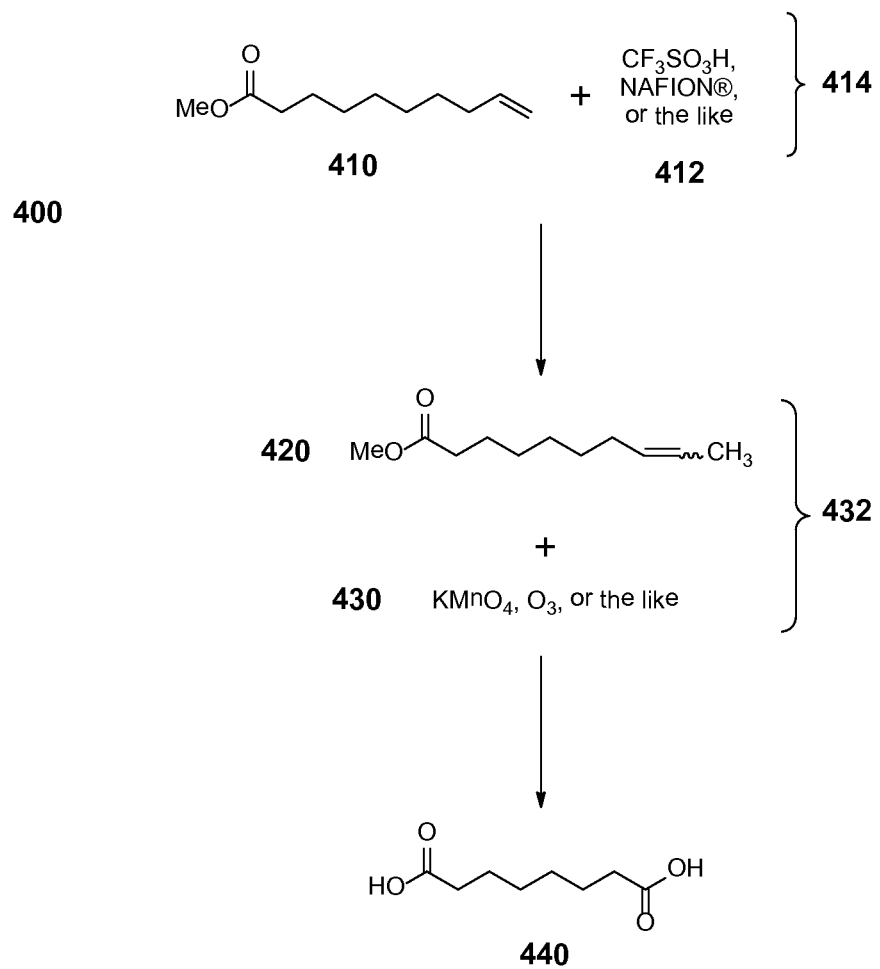
FIG. 4 depicts a representative reaction scheme for a transformation of 9-decenoic acid methyl ester (9-DAME) to suberic acid.

FIG. 4 depicts chemical structures and reaction schemes for an example of a method 400 of transforming 9-decenoic acid methyl ester (9-DAME) to suberic acid. Method 400 includes combining 9-decenoic acid methyl ester 410 and a fluorosulfonic acid 412 in a first reaction mixture 414, forming 8-decenoic acid methyl ester 420 from the 9-decenoic acid methyl ester 410, combining the 8-decenoic acid methyl ester 420 and an oxidizing agent 430 in a second reaction mixture 432, and forming suberic acid 440 from the 8-decenoic acid methyl ester 420. The fluorosulfonic acid 420 may be, for example trifluoromethane sulfonic acid, NAFION, or the like. The oxidizing agent 430 may be, for example, potassium permanganate, ozone, or the like.

Forming suberic acid using the above methods (i.e. as product 240, 340, or 440), may provide advantages over conventional methods of forming suberic acid. Conventional methods typically convert petrochemical reactants such as cyclooctene or cyclooctane into suberic acid through one or two oxidation steps. In contrast, the above methods can convert 9-DAME, which can be produced from renewable feedstocks, into suberic acid. The use of renewable feedstocks may advantageously provide simpler and/or more cost-effective production, reduced variability, improved sourcing, and increased biorenewability than the conventional methods.

Suberic acid formed from the above methods (i.e. as product 240, 340, or 440), may be used as a reactant to form a variety of products, including but not limited to lubricants, greases and polymers. One advantage of using suberic acid formed by the above methods is that molecules or materials may be formed from the suberic acid more economically and in larger quantities than was previously possible. Another advantage of using suberic acid formed by the above methods is that the resulting molecules or materials can have a higher percentage of their content from renewable sources.

In one example, suberic acid can be used to form a polyester. Polyesters formed from suberic acid and having molecular weights from 250 to 10,000 daltons may be used as lubricants. Polyesters formed from suberic acid and having higher molecular weights and/or including branching or crosslinking may be used as plastic materials. A polyester may be formed by polymerizing suberic acid and a monomer having two or more hydroxyl functional groups. Examples of di-hydroxyl functional monomers include but are not limited to ethylene glycol, diethylene glycol, triethylene glycol, tetraethylene glycol, propylene glycol, dipropylene glycol, tripropylene glycol, neopentyl glycol, 1,3-butanediol, 1,4-butanediol, 1,6-hexanediol, 1,4-di(2-hydroxyethyoxy)benzene, and the like, and combinations thereof.

A polyester may be formed by polymerizing suberic acid and a polyol having two or more hydroxyl functional groups. Examples of such polyols include but are not limited to poly(alkylene ether) polyols, polyester polyols, polycarbonate polyols having molecular weights from 250 to 10,000 daltons, and the like, and combinations thereof. Poly(alkylene ether) polyols may be formed, for example, by polymerizing cyclic ethers, glycols and dihydroxyethers. Examples of poly(alkylene ether) polyols include but are not limited to poly(propylene glycol) and polytetramethylene ether glycols (PTMEG). Polyester polyols may be formed, for example, by polymerizing caprolactone or by reacting dicarboxylic acids such as adipic, glutaric, sebacic and/or phthalic acid with diols such as ethylene glycol, 1,2-propylene glycol, 1,4-butylene glycol, diethylene glycol and/or 1,6-hexanediol, and/or with substances having three or more hydroxyl functional groups such as glycerol, trimethylolpropane, pentaerythritol and/or saccharides such as sorbitol. Examples of polyols include but are not limited to poly (diethylene glycol adipate).

In another example, suberic acid can be used to form a polyamide. A polyamide may be formed by polymerizing suberic acid and a monomer having two or more amine functional groups. Examples of amine functional monomers include but are not limited to alkyl and/or aromatic diamines, triamines, and tetramines. Specific examples of amine functional monomers include but are not limited to ethanediamine, triethylenetriamine, diethylenetriamine (DETA), hexamethylenetetramine, tetraethylenepentamine (TEPA), urea, and melamine. A polyamide may be formed by polymerizing suberic acid and a polyamine having two or more amine functional groups. Examples of such polyamines include but are not limited to amine-terminated polymers or prepolymers such as α-aminomethylethyl-ω-aminomethyl-ethoxy-poly[oxy(methyl-1,2-ethanediyl)].

Figure 5:
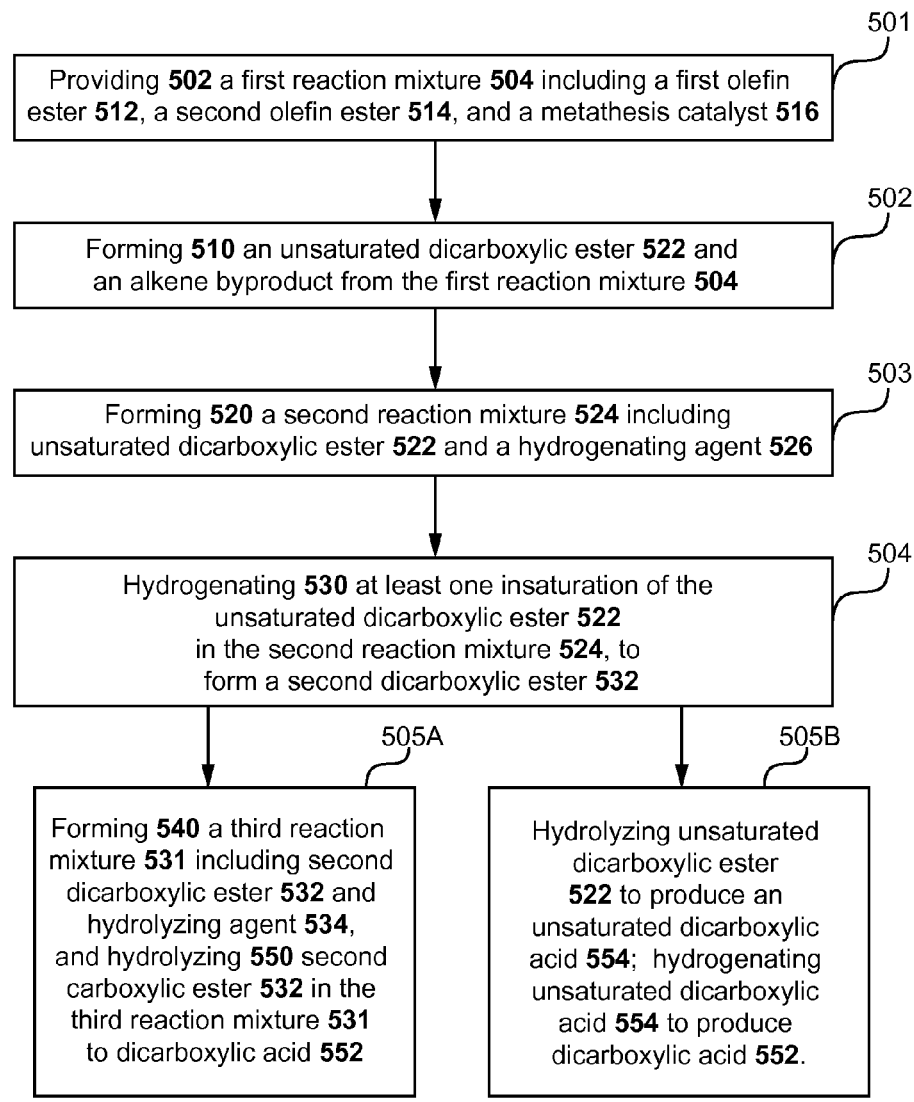
FIG. 5 represents a method of forming a dicarboxylic acid.

FIG. 5 represents a method 500 of forming a dicarboxylic acid. The method 500 includes providing 502 a first reaction mixture 504 including a first olefin ester 512, a second olefin ester 514, and a metathesis catalyst 516; forming 510 an unsaturated dicarboxylic ester 522 and an alkene byproduct from the first reaction mixture 504; forming 520 a second reaction mixture 524 including unsaturated dicarboxylic ester 522 and a hydrogenating agent 526; hydrogenating 530 at least one unsaturated group of the unsaturated dicarboxylic ester 522 in the second reaction mixture 524, to form a second dicarboxylic ester 532; forming 540 a third reaction mixture 531 including second dicarboxylic ester 532 and a hydrolyzing agent 534, and hydrolyzing 550 second carboxylic ester 532 in the third reaction mixture 531 to dicarboxylic acid 552. Alternatively, unsaturated dicarboxylic ester 522 may be hydrolyzed to produce an unsaturated dicarboxylic acid 554 which may be hydrogenated to produce dicarboxylic acid 552.

Metathesis catalyst 516 may be any suitable metathesis catalyst or metathesis catalyst system, such as those described above in conjunction with the production of terminal alkenyl group 110. In some instances, first olefin ester 512 and second olefin ester 514 are the same, which can be referred to as a "self-metathesis" reaction. In other instances, however, 512 and 514 are different, thereby giving rise to a cross-metathesis reaction. Other types of metathesis reactions are also known.

Example reactions of olefinic esters to make unsaturated dicarboxylic esters are described in PCT Publication WO 2008/140468, and United States Patent Application Publication Nos. 2009/0264672 and 2013/0085288, all three of which are hereby incorporated by reference as though fully set forth herein in their entireties, except that in the event of any inconsistent disclosure or definition from the present specification, the disclosure or definition herein shall be deemed to prevail.

In some embodiments, one or more of the reactants for the reaction(s) of 510 can be generated from a renewable source, e.g., by refining a natural oil or a derivative thereof. In some embodiments, the refining process includes cross-metathesizing the natural oil or a derivative thereof with an alkene. In such instances, the reactants may not be entirely pure, as certain other alkene and ester byproducts of the natural oil refining may be present in the input stream. Therefore, in some embodiments, the reactants can be subjected to a pre-treatment, such as a thermal pre-treatment, to remove certain impurities, including, but not limited to, water, volatile organics (esters and alkenes), and certain aldehydes.

Metathesis reactions can be carried out under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments where a reagent is supplied as a gas, an inert gaseous diluent can be used in the gas stream. In such embodiments, the inert atmosphere or inert gaseous diluent typically is an inert gas, meaning that the gas does not interact with the metathesis catalyst 516 to impede catalysis to a substantial degree. For example, non-limiting examples of inert gases or non-reactive gases include helium, neon, argon, nitrogen, methane (flared), and carbon dioxide, used individually or in with each other and other inert gases or non-reacting gases.

Metathesis reactions, including those disclosed herein, can be carried out in any suitable reactor, depending on a variety of factors. Relevant factors include, but are not limited to, the scale of the reaction, the selection of conditions (e.g., temperature, pressure, etc.) the identity of the reacting species, the identity of the resulting products and the desired product(s), and the identity of the metathesis catalyst 516. Suitable reactors can be designed by those of skill in the art, depending on the relevant factors, and incorporated into a reaction process such, such as those disclosed herein.

In certain embodiments, the metathesis catalyst 516 is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst 516 is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst 516 may be added in solid state form (and not slurried) to the natural oil or unsaturated ester (e.g., as an auger feed).

The metathesis reaction temperature may, in some instances, be a rate-controlling variable where the temperature of the first reaction mixture is brought to a metathesis reaction temperature that is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

The metathesis reaction can be run under any desired pressure. In some instances, it may be desirable to maintain the first reaction mixture a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than 70 atm (7000 kPa), or no more than 30 atm (3000 kPa). In some embodiments, the pressure for the metathesis reaction ranges from 1 atm (100 kPa) to 30 atm (3000 kPa).

A noted above, two or more olefin esters can be used to make a dibasic ester. In some embodiments, the first olefin ester 512 is a terminal olefin ester and the second olefin ester 514 is an internal olefin ester. In some such embodiments, the internal olefin ester 514 is formed by isomerizing a terminal olefin ester according to any of the embodiments disclosed above. For example, 9-decenoic acid esters produced from renewable feedstocks in a typical bio-refinery stream may be isomerized to 8-decenoic acid esters. In some alternative embodiments, the first olefin ester 512 and the second olefin ester 514 are both internal olefin esters. For example, when the internal olefin esters are both 8-decenoic acid esters, the resulting dibasic esters will be $C_{16}$-diesters. In some such embodiments, one or both of these internal olefin esters are formed by isomerizing a terminal olefin ester according to any of the embodiments disclosed above.

In some embodiments, the terminal olefin ester is a compound of formula (V):

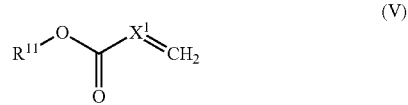

(V)

wherein:

$X^1$ is $C_{3-18}$ alkylene, $C_{3-18}$ alkenylene, $C_{2-18}$ heteroalkylene, or $C_{2-18}$ heteroalkenylene, each of which is optionally substituted one or more times by substituents selected independently from $R^{12}$;

$R^{11}$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^{12}$; and $R^{12}$ is a halogen atom, —OH, —NH$_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some such embodiments, $X^1$ is $C_{3-18}$ alkylene, $C_{3-18}$ alkenylene, or $C_{2-18}$ oxyalkylene, each of which is optionally substituted one or more times by substituents selected from the group consisting of a halogen atom, —OH, —O($C_{1-6}$ alkyl), —NH$_2$, —NH($C_{1-6}$ alkyl), and N($C_{1-6}$ alkyl)$_2$. In some further embodiments, $X^1$ is $C_{3-18}$ alkylene, $C_{3-18}$ alkenylene, or $C_{2-18}$ oxyalkylene, each of which is optionally substituted one or more times by —OH. In some even further embodiments, $X^1$ is —(CH$_2$)$_2$—CH=, —(CH$_2$)$_3$—CH=, —(CH$_2$)$_4$—CH=, —(CH$_2$)$_5$—CH=, —(CH$_2$)$_6$—CH=, —(CH$_2$)$_7$—CH=, —(CH$_2$)$_8$—CH=, —(CH$_2$)$_9$—CH=, —(CH$_2$)$_{10}$—CH=, —(CH$_2$)$_{11}$—CH=, —(CH$_2$)$_{12}$—CH=, —(CH$_2$)$_{13}$—CH=, —(CH$_2$)$_{14}$—CH=, or —(CH$_2$)$_{15}$—CH=. In some even further embodiments, $X^1$ is —(CH$_2$)$_7$—CH=.

In some such embodiments, $R^{11}$ is $C_{1-8}$ alkyl, $C_{2-8}$ alkenyl, or $C_{1-8}$ oxyalkyl, each of which is optionally substituted one or more times by —OH. In some further embodiments, $R^{11}$ is methyl, ethyl, propyl, isopropyl, butyl, isobutyl, sec-butyl, tert-butyl, pentyl, tert-pentyl, neopentyl, hexyl, or 2-ethylhexyl. In some even further embodiments, $R^{11}$ is methyl.

In some embodiments, the terminal olefin ester is 9-deneoic acid alkyl ester, such as 9-decenoic acid methyl ester.

In some other embodiments, the first olefin ester 512 and the second olefin ester 514 are both internal olefin esters. In some such embodiments, the first olefin ester 512 and the second olefin ester 514 are independently compounds of formula (VI):

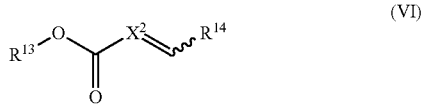

(VI)

where:

$X^2$ is $C_{3-18}$ alkylene, $C_{3-18}$ alkenylene, $C_{2-18}$ heteroalkylene, or $C_{2-18}$ heteroalkenylene, each of which is optionally substituted one or more times by substituents selected independently from $R^{15}$;

$R^{13}$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^{15}$;

$R^{14}$ is a halogen atom, —OH, —NH$_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl; and $R^{15}$ is a halogen atom, —OH, —NH$_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some such embodiments, $X^2$ is $C_{3-18}$ alkylene, $C_{3-18}$ alkenylene, or $C_{2-18}$ oxyalkylene, each of which is optionally substituted one or more times by substituents selected from the group consisting of a halogen atom, —OH, —O($C_{1-6}$ alkyl), —NH$_2$, —NH($C_{1-6}$ alkyl), and N($C_{1-6}$ alkyl)$_2$. In some further such embodiments, $X^2$ is $C_{3-18}$ alkylene, $C_{3-18}$ alkenylene, or $C_{2-18}$ oxyalkylene, each of which is optionally substituted one or more times by —OH. In some even further such embodiments, $X^2$ is —(CH$_2$)$_2$—CH=, —(CH$_2$)$_3$CH=, —(CH$_2$)$_4$—CH=, —(CH$_2$)$_5$—CH=, —(CH$_2$)$_6$—CH=, —(CH$_2$)$_7$—CH=, —(CH$_2$)$_8$—CH=, —(CH$_2$)$_9$—CH=, —(CH$_2$)O—CH=, —(CH$_2$)$_{11}$—CH=, —(CH$_2$)$_{12}$—CH=, —(CH$_2$)$_{13}$—CH=, —(CH$_2$)$_{14}$—CH=, or —(CH$_2$)$_{15}$—CH=. In some such embodiments, $X^2$ is —(CH$_2$)$_6$—CH=.

In some such embodiments, $R^{13}$ is $C_{1-8}$ alkyl, $C_{2-8}$ alkenyl, or $C_{1-8}$ oxyalkyl, each of which is optionally substituted one or more times by —OH. In some further such embodiments, $R^{13}$ is methyl, ethyl, propyl, isopropyl, butyl, isobutyl, sec-butyl, tert-butyl, pentyl, tert-pentyl, neopentyl, hexyl, or 2-ethylhexyl. In some even further such embodiments, $R^{13}$ is methyl.

In some such embodiments, $R^{14}$ is $C_{1-8}$ alkyl, $C_{2-8}$ alkenyl, or $C_{1-8}$ oxyalkyl, each of which is optionally substituted one or more times by —OH. In some further such embodiments, $R^{14}$ is methyl, ethyl, propyl, butyl, pentyl, hexyl, heptyl, octyl, or nonyl. In some even further such embodiments, $R^{14}$ is methyl or ethyl. In some embodiments, $R^{14}$ is methyl.

In some embodiments, the internal olefin ester is an 8-decenoic acid alkyl ester, such as 8-decenoic acid methyl ester. In some such embodiments, the ester of 8-decenoic acid is formed by isomerizing an ester of 9-decenoic acid.

The hydrogenating 530 of at least one unsaturated group in the unsaturated dicarboxylic ester 522 may be carried with any suitable hydrogenating agent 526. In certain embodiments, hydrogen gas is reacted with the unsaturated dicarboxylic ester 522 in the presence of a hydrogenation catalyst to form a saturated dicarboxylic acid, for example, in a hydrogenation reactor. Any suitable hydrogenation catalyst can be used. In some embodiments, the hydrogenation catalyst comprises nickel, copper, palladium, platinum, molybdenum, iron, ruthenium, osmium, rhodium, or iridium, individually or in any combinations thereof. Such catalysts may be heterogeneous or homogeneous. In some embodiments, the catalysts are supported nickel or sponge nickel type catalysts. In some embodiments, the hydrogenation catalyst comprises nickel that has been chemically reduced with hydrogen to an active state (i.e., reduced nickel) provided on a support. The support may comprise porous silica (e.g., kieselguhr, infusorial, diatomaceous, or siliceous earth) or alumina. The catalysts are characterized by a high nickel surface area per gram of nickel. Commercial examples of supported nickel hydrogenation catalysts include those available under the trade designations NYSOFACT, NYSOSEL, and NI 5248 D (from BASF Catalysts LLC, Iselin, N.J.). Additional supported nickel hydrogenation catalysts include those commercially available under the trade designations PRICAT Ni 62/15 P, PRICAT Ni 55/5, PPRICAT 9910, PRICAT 9920, PRICAT 9908, PRICAT 9936 (from Johnson Matthey Catalysts, Ward Hill, Mass.).

The supported nickel catalysts may be of the type described in U.S. Pat. Nos. 3,351,566, 6,846,772, European Patent Publication No. 0168091, and European Patent Publication No. 0167201, each of which are incorporated by reference herein in their entireties, except that in the event of any inconsistent disclosure or definition from the present specification, the disclosure or definition herein shall be deemed to prevail. Hydrogenation may be carried out in a batch or in a continuous process and may be partial hydrogenation or complete hydrogenation. In certain embodiments, the temperature ranges from 50° C. to 350° C., 100° C. to 300° C., 150° C. to 250° C., or 100° C. to 150° C. The desired temperature may vary, for example, with hydrogen gas pressure. Typically, a higher gas pressure will require a lower temperature. Hydrogen gas is pumped into the reaction vessel to achieve a desired pressure of $H_2$ gas. In certain embodiments, the $H_2$ gas pressure ranges from 15 psig (1 barg) to 3000 psig (204.1 barg), 15 psig (1 barg) to 90 psig (6.1 barg), or 100 psig (6.8 barg) to 500 psig (34 barg). As the gas pressure increases, more specialized high-pressure processing equipment may be required. In certain embodiments, the reaction conditions are "mild", wherein the temperature is between 50° C. and 100° C. and the $H_2$ gas pressure is less than 100 psig. In other embodiments, the temperature is between 100° C. and 150° C., and the pressure is between 100 psig (6.8 barg) and 500 psig (34 barg). When the desired degree of hydrogenation is reached, the reaction mass is cooled to the desired filtration temperature.

The amount of hydrogenation catalyst is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the $H_2$ gas pressure. In some embodiments, the hydrogenation catalyst is used in an amount of 10 percent by weight or less, for example, 5 percent by weight or less or 1 percent by weight or less.

The products of the forming 510 of unsaturated dicarboxylic ester 522 can contain various impurities. These impurities can be compounds that were made by various kinds of unproductive metathesis. Or, in some instances, the impurities may result from the presence of impurities in the starting compositions. In any event, it can, in some embodiments, be desirable to strip out and/or distill out 560 these impurities. In some such embodiments, the stripping and/or distilling can occur after 510, but before the hydrogenating 530. In some alternative embodiments, the stripping and/or distilling can occur after both 510 and the hydrogenating 530. These impurities may contain more esters than hydrocarbons (e.g., monobasic esters), as certain alkene impurities can be vented out of the reactor during the metathesis reaction, e.g., due to the lower relative boiling point of the alkene impurities. Of course, in some instances, these alkene impurities may stay in the reactor long enough to involve themselves in certain metathesis reactions, thereby generating other impurities (e.g., an additional alkene impurity and an additional ester impurity). Paraffin impurities can also be present, which can be removed by the stripping and/or distilling 560, for example, after hydrogenation.

In some embodiments, the stripping and/or distilling 560 may lead to the removal of certain amounts of the first olefin ester 512 and/or the second olefin ester 514. In some such embodiments, these stripped out reactants can be collected and reused for further metathesis reactions.

In some embodiments, it may be desirable to further purify the second dicarboxylic ester 532 prior to the hydrolyzing 550. For example, in some embodiments, the second dicarboxylic ester 532 can be recrystallized. The recrystallization can be carried out by any suitable technique. The second dicarboxylic ester 532 may be dissolved in a solvent system, for example, with heating, followed by cooling until solid crystals of the second dicarboxylic ester 532 appear. This can be a suitable means of removing impurities that are more soluble in the solvent system than the second dicarboxylic ester 532, e.g., shorter-chain monobasic and dicarboxylic esters and/or acids.

The hydrolizyng 550 second dicarboxylic ester 532 to a dicarboxylic acid 552 can be carried out by any suitable hydrolyzing agents. In some embodiments, the second dicarboxylic ester 532 is converted to dicarboxylic acid 552 by saponification, followed by acidification. In some embodiments, the dicarboxylic acid 552 is a compound having the formula: H—OOC—Y—COO—H, wherein Y denotes any organic moiety (such as hydrocarbyl or silyl groups), including those bearing heteroatom containing substituent groups. In some such embodiments, Y is a divalent hydrocarbyl group, which can be optionally substituted with heteroatom-containing substituents, or whose carbon atoms can be replaced by one or more heteroatoms. Such divalent hydrocarbyl groups can include substituted and unsubstituted alkylene, alkenylene, and oxyalkylene groups.

In some embodiments, the dicarboxylic acid 552 is a compound of formula (II):

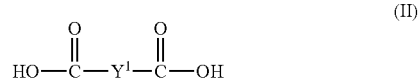

(II)

wherein, $Y^1$ is $C_{6-36}$ alkylene or $C_{6-36}$ heteroalkylene, each of which is optionally substituted one or more times by substituents selected independently from $R^3$; and $R^3$ is a halogen atom, —OH, —NH$_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $Y^1$ is $C_{6-36}$ alkylene or $C_{4-36}$ oxyalkylene, each of which is optionally substituted one or more times by substituents selected from the group consisting of a halogen atom, —OH, —O($C_{1-6}$ alkyl), —NH$_2$, —NH($C_{1-6}$ alkyl), and N($C_{1-6}$ alkyl)$_2$. In some further such embodiments, $Y^1$ is $C_{6-36}$ alkylene, $C_{6-36}$ alkenylene, or $C_{4-36}$ oxyalkylene, each of which is optionally substituted one or more times by —OH. In some further such embodiments, $Y^1$ is —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$—, —(CH$_2$)$_{20}$—, —(CH$_2$)$_{21}$—, or —(CH$_2$)$_{22}$—.

In some embodiments, the dicarboxylic acid 552 can be further purified. In some embodiments, the purification is carried out using the recrystallization methods described above.

The reactions of method 500 may lead to the production of colored impurities. As used herein, the term "colored impurities" refers to compounds that absorb light having a wavelength of 440 nm or 550 nm. Thus, these are compounds that absorb light in the blue-violet or the green portions of the visible electromagnetic spectrum. In some embodiments, the mole-to-mole ratio of formed dicarboxylic acids to colored impurities is at least 250:1, or at least 350:1, or at least 500:1, or at least 1000:1, or at least 2000:1. In some embodiments, a composition including dicarboxylic acid 552 can be treated to lower even further the concentration of colored impurities in the composition. For example, in some such embodiments, the composition can be decolorized, for example, by contacting the composition with a decolorizing agent. Suitable decolorizing agents include, but are not limited to, activated carbon, silica, silicates (e.g., magnesium silicates), clay, diatomaceous earth, and alumina. In some embodiments, for example, decolorizing agent is added to the composition, and the decolorizing agent is subsequently filtered out. Or, in some alternative embodiments, the composition can be passed through a bed containing the decolorizing agent. Additional treatments can also be carried out, either in addition to decolorization or instead of decolorization. In some embodiments, the composition can be treated with a bleaching agent (e.g., an oxidizing agent), followed by an extraction to remove the bleaching agent from the composition.

Figure 6:
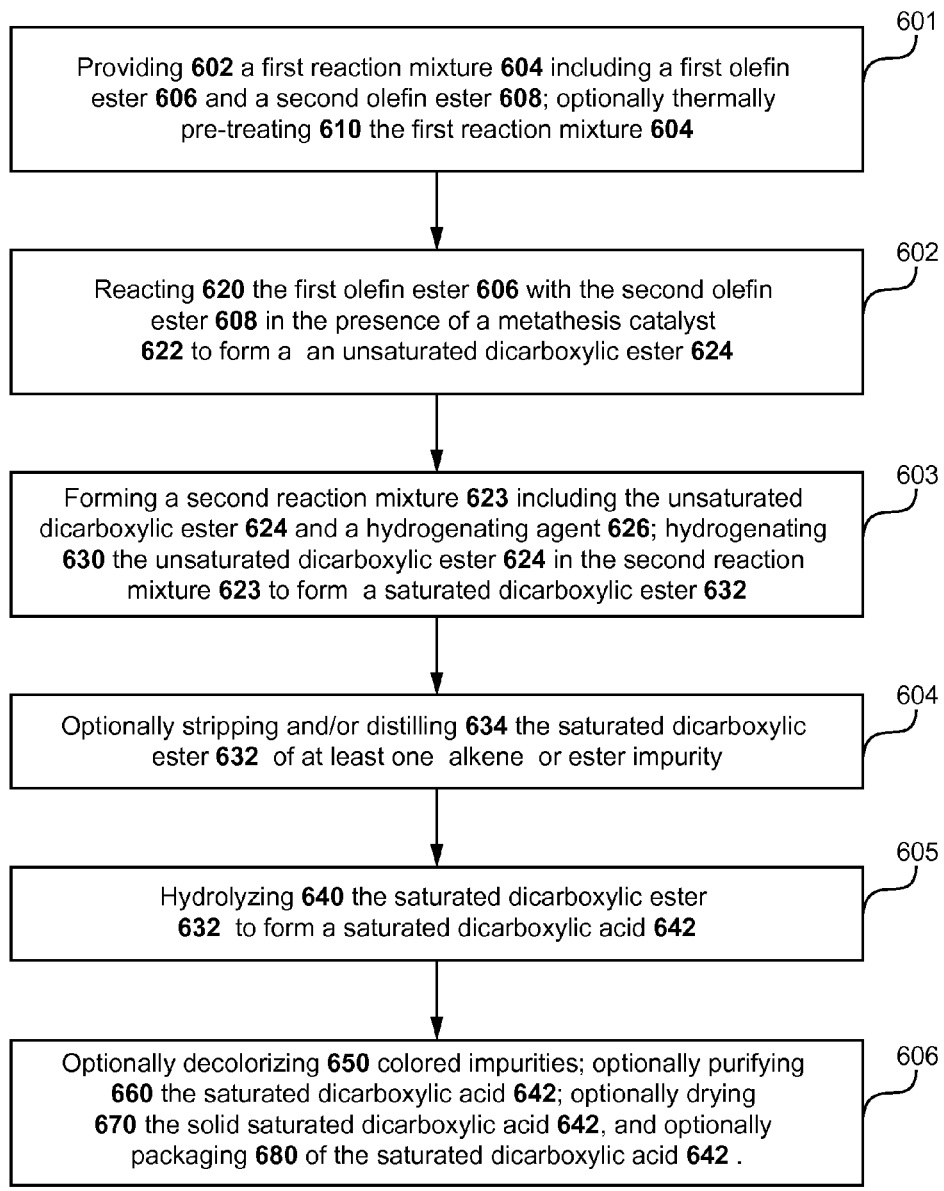
FIG. 6 represents a method of forming a dicarboxylic acid.

FIG. 6 shows an illustrative embodiment for forming a dicarboxylic acid. The method 600 includes: providing 602 a first reaction mixture 604 including a first olefin ester 606 and a second olefin ester 608; optionally thermally pretreating 610 the first reaction mixture 604; reacting 620 the first olefin ester 606 with the second olefin ester 608 in the presence of a metathesis catalyst 622 to form an unsaturated dicarboxylic ester 624; forming a second reaction mixture 623 including the unsaturated dicarboxylic ester 624 and a hydrogenating agent 626; hydrogenating 630 the unsaturated dicarboxylic ester 624 in the second reaction mixture 623 to form a saturated dicarboxylic ester 632 (including optional recovery of a hydrogenation catalyst, e.g., by filtration); optionally stripping and/or distilling 634 the saturated dicarboxylic ester 632 of at least one alkene or ester impurity; hydrolyzing 640 the saturated dicarboxylic ester 632 to form a saturated dicarboxylic acid 642; optionally decolorizing 650 colored impurities (including optional recovery of a decolorizing agent); optionally purifying 660 the saturated dicarboxylic acid 642 (e.g., by recrystallization); optionally drying 670 the solid saturated dicarboxylic acid 642; and optionally packaging 680 of the saturated dicarboxylic acid 642. In some embodiments, the saturated dicarboxylic acid 642 is hexadecanedioic acid. In some such embodiments, the first olefin ester 606 and second olefin ester 608 both are 9-decenoic acid methyl ester. In some other such embodiments, the first olefin ester 606 and the second olefin ester 608 are both 9-dodecenoic acid methyl ester. In some even further such embodiments, the first olefin ester 606 is 9-decenoic acid methyl ester and the second olefin ester 608 is 9-dodecenoic acid methyl ester. In additional embodiments, the first olefin ester 606 and the second olefin ester 608 are both 8-decenoic acid methyl ester (8-DAME).

Figure 7:
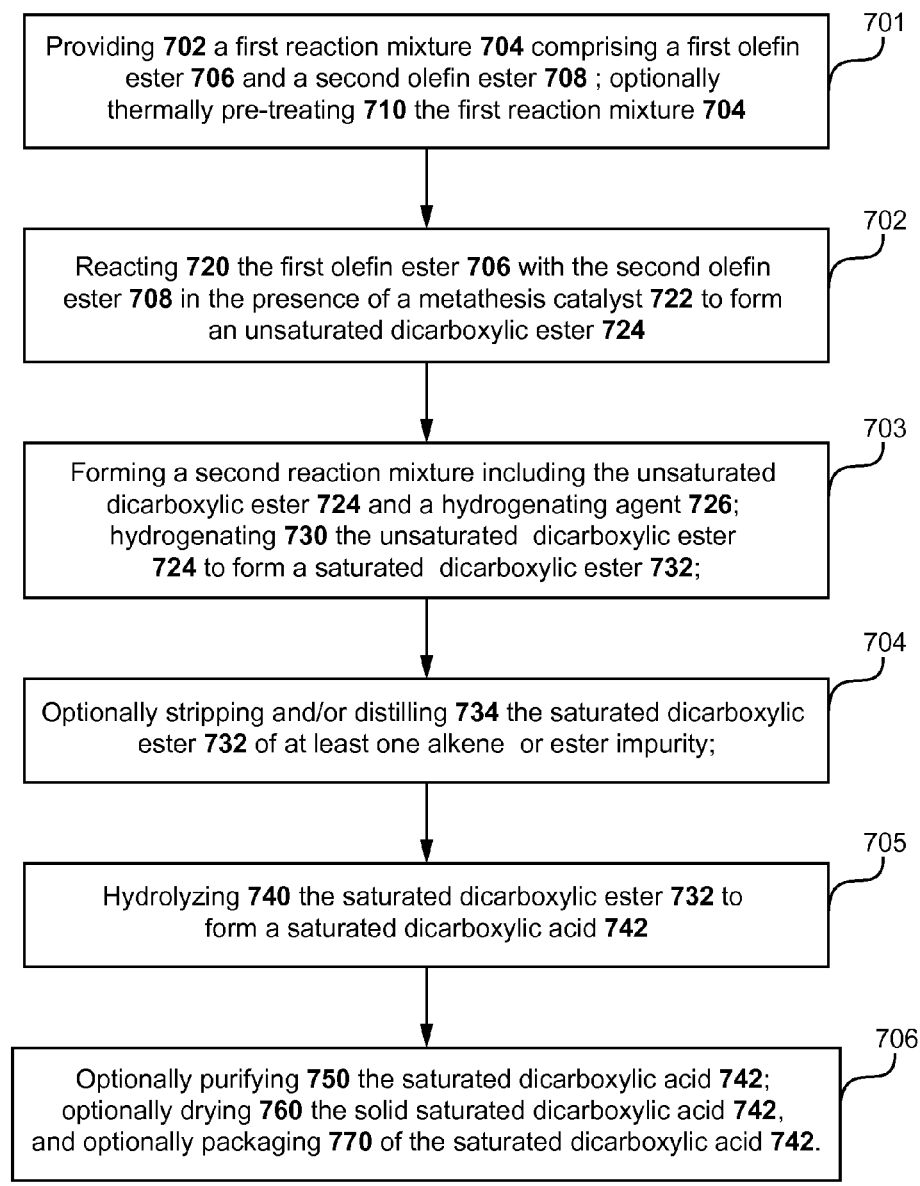
FIG. 7 represents a method of forming a dicarboxylic acid.

FIG. 7 shows an illustrative embodiment for forming a dicarboxylic acid. The method 700 includes: providing 702 a first reaction mixture 704 comprising a first olefin ester 706 and a second olefin ester 708; optionally thermally pretreating 710 the first reaction mixture 704; reacting 720 the first olefin ester 706 with the second olefin ester 708 in the presence of a metathesis catalyst 722 to form an unsaturated dicarboxylic ester 724; forming a second reaction mixture including the unsaturated dicarboxylic ester 724 and a hydrogenating agent 726; hydrogenating 730 the unsaturated dicarboxylic ester 724 to form a saturated dicarboxylic ester 732 (including optional recovery of a hydrogenation catalyst, e.g., by filtration); optionally stripping and/or distilling 734 the saturated dicarboxylic ester 732 of at least one alkene or ester impurity; hydrolyzing 740 the saturated dicarboxylic ester 732 to form a saturated dicarboxylic acid 742; optionally purifying 750 the saturated dicarboxylic acid 742 (e.g., by recrystallization); optionally drying 760 the solid saturated dicarboxylic acid 742; and optionally packaging 770 of the saturated dicarboxylic acid 742. In some embodiments, the saturated dicarboxylic acid 742 is hexadecanedioic acid. In some such embodiments, the first olefin ester 706 and second olefin ester 708 both are 9-decenoic acid methyl ester. In some other such embodiments, the first olefin ester 706 and the second olefin ester 708 both are 9-dodecenoic acid methyl ester. In some even further such embodiments, the first olefin ester 706 is 9-decenoic acid methyl ester and the second olefin ester 708 is 9-dodecenoic acid methyl ester. In additional embodiments, the first olefin ester 706 and the second olefin ester 708 are both 8-DAME.

Figure 8:
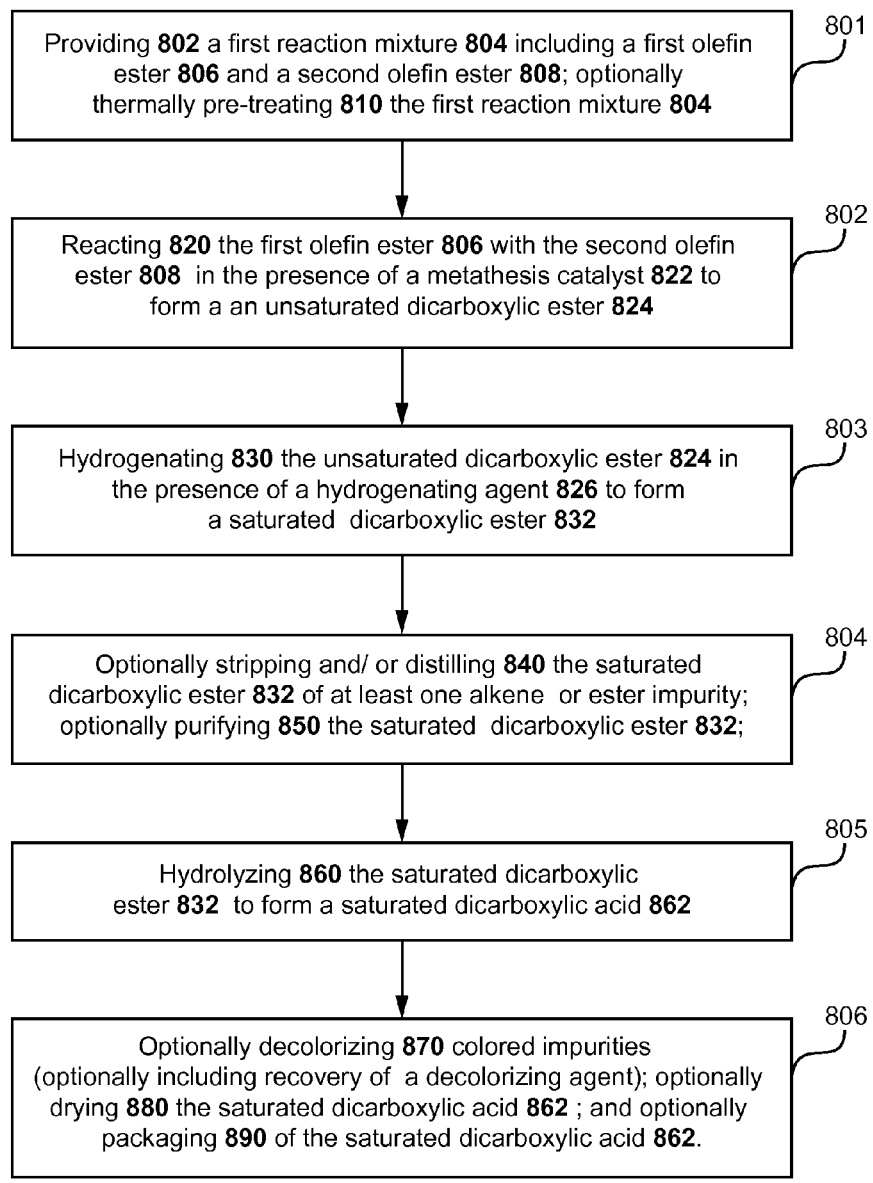
FIG. 8 represents a method of forming a dicarboxylic acid.

FIG. 8 shows an illustrative embodiment for forming a dicarboxylic acid. The method 800 includes: providing 802 a first reaction mixture 804 including a first olefin ester 806 and a second olefin ester 808; optionally thermally pretreating 810 the first reaction mixture 804; reacting 820 the first olefin ester 806 with the second olefin ester 808 in the presence of a metathesis catalyst 822 to form an unsaturated dicarboxylic ester 824; hydrogenating 830 the unsaturated dicarboxylic ester 824 in the presence of a hydrogenating agent 826 to form a saturated dicarboxylic ester 832 (including optional recovery of a hydrogenation catalyst, e.g., by filtration); optionally stripping and/or distilling 840 the saturated dicarboxylic ester 832 of at least one alkene or ester impurity; optionally purifying 850 the saturated dicarboxylic ester 832, e.g., by recrystallization; hydrolyzing 860 the saturated dicarboxylic ester 832 to form a saturated dicarboxylic acid 862; optionally decolorizing 870 colored impurities (optionally including recovery of a decolorizing agent); optionally drying 880 the saturated dicarboxylic acid 862; and optionally packaging 890 of the saturated dicarboxylic acid 862. In some embodiments, the saturated dicarboxylic acid 862 is hexadecanedioic acid. In some such embodiments, the first olefin ester 806 and second olefin ester 808 both are 9-decenoic acid methyl ester. In some other such embodiments, the first olefin ester 806 and the second olefin ester 808 are both 9-dodecenoic acid methyl ester. In some even further such embodiments, the first olefin ester 806 is 9-decenoic acid methyl ester and the second olefin ester 808 is 9-dodecenoic acid methyl ester. In additional embodiments, the first olefin ester 806 and the second olefin ester 808 are both 8-DAME.

Figure 9:
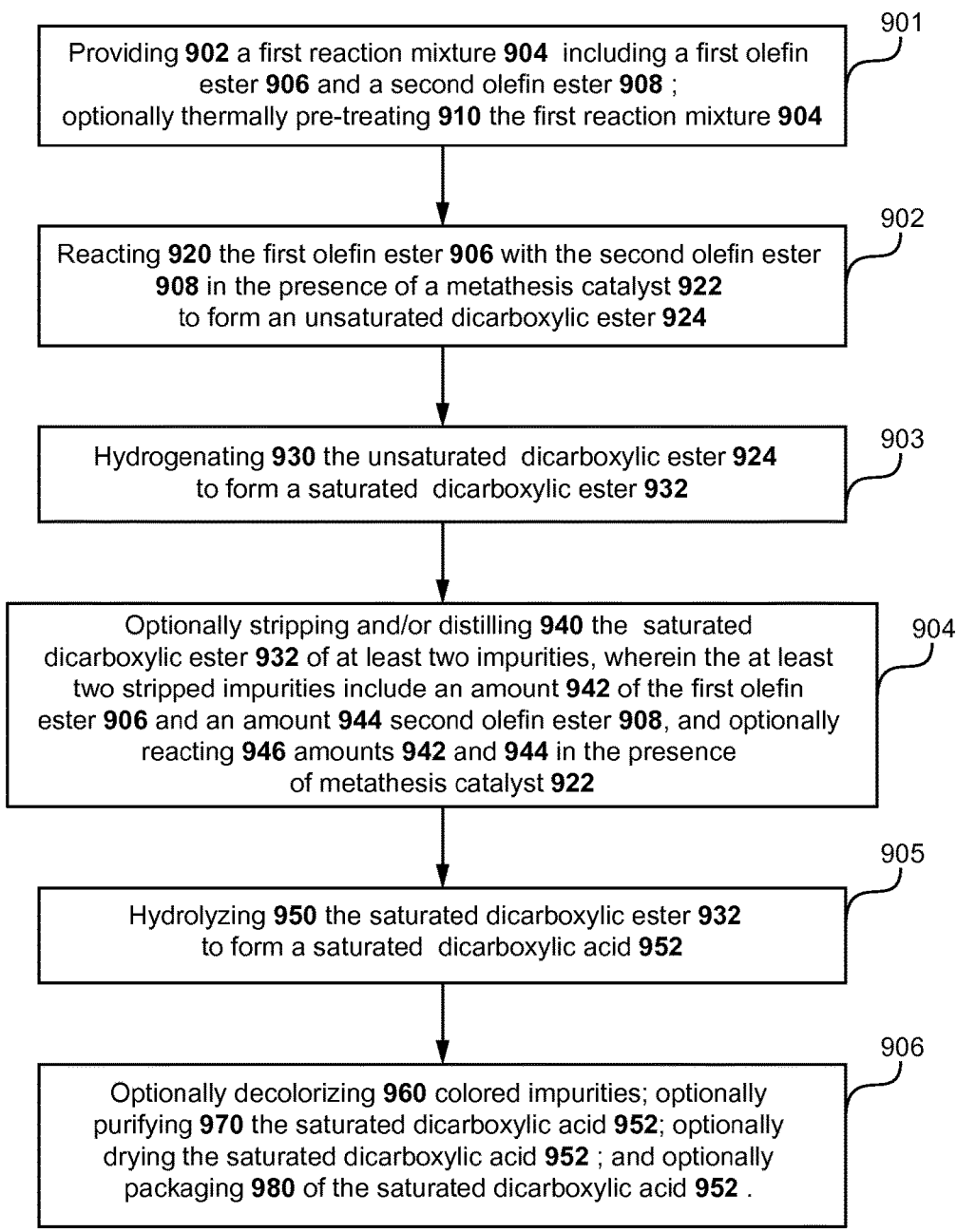
FIG. 9 represents a method of forming a dicarboxylic acid.

FIG. 9 shows an illustrative embodiment for forming a dicarboxylic acid. The method 900 includes: providing 902 a first reaction mixture 904 including a first olefin ester 906 and a second olefin ester 908; optionally thermally pretreating 910 the first reaction mixture 904; reacting 920 the first olefin ester 906 with the second olefin ester 908 in the presence of a metathesis catalyst 922 to form an unsaturated dicarboxylic ester 924; hydrogenating 930 the unsaturated dicarboxylic ester 924 to form a saturated dicarboxylic ester 932 (including optional recovery of a hydrogenation catalyst, e.g., by filtration); optionally stripping and/or distilling 940 the saturated dicarboxylic ester 932 of at least two impurities, wherein the at least two stripped impurities include an amount 942 of the first olefin ester 906 and an amount 944 second olefin ester 908, and optionally reacting 946 amounts 942 and 944 in the presence of metathesis catalyst 922; hydrolyzing 950 the saturated dicarboxylic ester 932 to form a saturated dicarboxylic acid 952; optionally decolorizing 960 colored impurities (including optional recovery of a decolorizing agent); optionally purifying 970 the saturated dicarboxylic acid 952 (e.g., by recrystallization); optionally drying the saturated dicarboxylic acid 952; and optionally packaging 980 of the saturated dicarboxylic acid 952. In some embodiments, the saturated dicarboxylic acid 952 is octadecanedioic acid. In some such embodiments, the first olefin ester 906 and second olefin ester 908 both are 9-decenoic acid methyl ester. In some other such embodiments, the first olefin ester 906 and the second olefin ester 908 are both 9-dodecenoic acid methyl ester. In some even further such embodiments, the first olefin ester 906 is 9-decenoic acid methyl ester and the second olefin ester 908 is 9-decenoic acid methyl ester. In additional embodiments, the first olefin ester 906 and the second olefin ester 908 are both 8-DAME.

In some embodiments, an 8-decenoic acid alkyl ester (8-DAAE), such as 8-DAME, is reacted with itself or another olefin ester in a metathesis reaction to form an unsaturated dicarboxylic ester that may be hydrogenated and hydrolyzed to produce a dicarboxylic acid. In some such embodiments, the other olefin ester is one of formula (V) or (VI), above. In order to obtain dicarboxylic acids featuring relatively longer carbon chains, e.g. chains having from 16 to 36 carbon atoms, the other olefin ester preferably features at least 8 carbon atoms, e.g. an olefin ester of formula (V), where $X^1$ is $C_{8-18}$ alkylene or $C_{3-18}$ alkenylene, or an olefin ester of formula (VI), where $X^2$ is $C_{8-18}$ alkylene or $C_{3-18}$ alkenylene.

The olefin esters employed above can, in certain embodiments, be derived from renewable sources, such as various natural oils. Any suitable methods can be used to make these compounds from such renewable sources. Suitable methods include, but are not limited to, fermentation, conversion by bioorganisms, and conversion by metathesis. In some embodiments, natural oils can be subjected to various pre-treatment processes, which can facilitate their utility for use in certain metathesis reactions. Useful pre-treatment methods are described in United States Patent Application Publication No. 2011/0113679 and U.S. Provisional Patent Application Nos. 61/783,321 and 61/783,720, both filed Mar. 14, 2013, all three of which are incorporated by reference herein in their entirety, except that in the event of any inconsistent disclosure or definition from the present specification, the disclosure or definition herein shall be deemed to prevail.

In some embodiments, after any optional pre-treatment of the natural oil feedstock, the natural oil feedstock is reacted in the presence of a metathesis catalyst in a metathesis reactor. In some other embodiments, an olefin ester (e.g., an unsaturated glyceride, such as an unsaturated triglyceride) is reacted in the presence of a metathesis catalyst in a metathesis reactor. The olefin ester may be a component of the natural oil feedstock, or may be derived from other sources, e.g., from esters generated in earlier-performed metathesis reactions. In certain embodiments, in the presence of a metathesis catalyst, the natural oil or olefin ester can undergo a self-metathesis reaction with itself. In other embodiments, the natural oil or olefin ester undergoes a cross-metathesis reaction with an olefin. The self-metathesis and/or cross-metathesis reactions form a metathesized product wherein the metathesized product comprises olefins and esters.

The following examples are provided to illustrate one or more preferred embodiments of the invention. Numerous variations can be made to the following examples that lie within the scope of the invention.

EXAMPLES

Example 1: Isomerization of 9-decenoic acid methyl ester (9-DAME)

A reaction mixture was prepared by combining 100 g 9-decenoic acid methyl ester (9-DAME; Elevance Renewable Sciences, Inc., Woodridge, Ill.) with 2.5 g of trifluoromethanesulfonic acid (Aldrich; St. Louis, Mo.), providing an acid content of 2.5 wt %. The reaction mixture was heated to 60° C. and stirred for 17 hours, and then stirred as it cooled to room temperature. The reaction mixture was washed with 50 mL of a saturated aqueous solution of sodium bicarbonate. The organic phase from the washing was dried with magnesium sulfate and filtered. The product was then distilled at 3 Torr, with the major fraction (85 g) of a clear, colorless liquid collected at a pot temperature of 103-120° C., and a head temperature of 95-100° C.

The product was characterized by nuclear magnetic resonance (NMR) using a Varian Inova 400 and $CDCl_3$ solvent. $^1H$ NMR (400 megahertz (MHz)) and $^{13}C$ NMR (100 MHz) spectra were consistent with a product mixture containing mostly 8-decenoic acid methyl ester (8-DAME), as well as small amounts of 7-decenoic acid methyl ester (7-DAME) and 6-decenoic acid methyl ester (6-DAME) byproducts, and of 9-DAME starting material.

The product was characterized by gas chromatography/mass spectrometry. Prior to characterization, the product was combined with dimethyl disulfide and iodine ($I_2$) to convert the carbon-carbon double bonds in the product into α,β-bis-methylthioether groups, following the method of Shibahara, A. et al., *J. Am. Oil Chem. Soc.*, 85, 93-94 (2008). This conversion of the double bonds allowed for quantification of the relative amounts of 8-DAME, 7-DAME, 6-DAME, and 9-DAME in the product mixture.

Table 1 lists the substances identified in the product mixture using NMR and GC/MS. The overall conversion of the 9-DAME into an isomer was 95.6% (95.6%=100%−(1.3%+3.8%+4.3%+17.7%+19.9%+48.6%)). The yield of 8-DAME, including both cis- and trans-isomers, was 68.5% (68.5%=19.9%+48.6%). Of the isomers produced, 8-DAME constituted 72% of the isomerized product (71.7%=100%×(19.9%+48.6%)/(1.3%+3.8%+4.3%+17.7%+19.9%+48.6%)).

TABLE 1

Substances in isomerization reaction product mixture.

| | | Concentration in product mixture (%) | |
|---|---|---|---|
| | | cis- | trans- |
| 6-DAME | 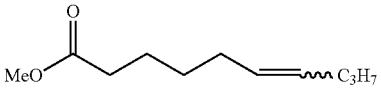 | 1.3 | 3.8 |
| 7-DAME | 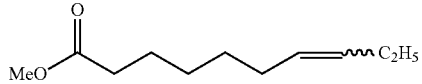 | 4.3 | 17.7 |

TABLE 1-continued

Substances in isomerization reaction product mixture.

| | Concentration in product mixture (%) | |
|---|---|---|
| | cis- | trans- |
| 8-DAME (MeO-C(O)-(CH2)6-CH=CH-CH3) | 19.9 | 48.6 |
| 9-DAME (MeO-C(O)-(CH2)7-CH=CH2) | | 4.0 |

Example 2: Isomerization of 9-DAME Using Other Reaction Conditions

The effects of reaction temperature, reaction time, type of acid, and amount of acid on the isomerization of 9-DAME were investigated by performing the reaction under a variety of different reaction conditions. Each reaction mixture was prepared by combining 100 g 9-DAME with either trifluoromethanesulfonic acid or a NAFION resin. The NAFION resin used was SAC-13 (Aldrich), which is a fluorosulfonic acid polymer on amorphous silica at a loading of 10-20%, having an average pore volume greater than 0.6 mL/g, an average pore diameter greater than 10 nm, a surface area greater than 200 m²/g and a density of 2.1 g/mL at 25° C.

Table 2 lists the reactants present in the different reaction mixtures, the reaction temperatures and times, and the percent conversion of 9-DAME into an isomer product. The products were isolated and characterized by NMR as described in Example 1.

TABLE 2

Reactants and reaction conditions for isomerization reactions.

| Acid used | Acid loading (%) | Temperature (° C.) | Time (hours) | Conversion of 9-DAME (%) |
|---|---|---|---|---|
| TfOH* | 2.5 | 60 | 17 | 95 |
| TfOH | 2.5 | 20 | 72 | <10 |
| TfOH | 1 | 60 | 18 | 50 |
| TfOH | 1 | 90 | 18 | >90 |
| NAFION | 5 | 60 | 18 | <10 |
| NAFION | 5 | 120 | 6 | >98 |

*Trifluoromethanesulfonic acid

Example 3: Isomerization of 1-decene

A reaction mixture was prepared by combining 100 g 1-decene with 2.5 g of trifluoromethanesulfonic acid, providing an acid content of 2.5 wt %. The reaction mixture was heated to 60° C. and stirred for 17 hours, and then stirred as it cooled to room temperature. The products were isolated and characterized by NMR and GC/MS as described in Example 1. The overall conversion of 1-decene into an isomer was 60%. Of the isomers produced, 2-decene (both cis- and trans-isomers) constituted over 70% of the isomerized product.

Example 4: Oxidation of 8-decenoic acid methyl ester (8-DAME)

A reaction mixture is prepared by combining 8-decenoic acid methyl ester and water. The oxidizing agent $KMnO_4$ is then added, and the reaction mixture is heated and stirred. Suberic acid is formed by oxidative cleavage of the carbon-carbon double bond, and by hydrolysis of the methyl ester group.

Alternatively, a reaction mixture is prepared by combining 8-decenoic acid methyl ester and water, and then ozone ($O_3$) is bubbled through the reaction mixture as the reaction mixture is heated and stirred. Suberic acid is formed by oxidative cleavage of the carbon-carbon double bond, and by hydrolysis of the methyl ester group.

Example 5

A reaction mixture is prepared by combining 8-decenoic acid methyl ester, Hoveyda-Grubbs' catalyst, and dicloromethane. The reaction mixture is then heated and stirred. Dimethyl hexadec-8-enedioate and 2-butene are formed by metathesis of the 8-decenoic acid methyl ester; the hexadec-8-enedioate is then converted to hexadecanedioic acid following hydrogenation of the carbon-carbon double bond and hydrolysis of the methyl ester groups.

Another reaction mixture is prepared by combining 8-decenoic acid methyl ester, 9-undecanoic methyl ester, Hoveyda-Grubbs' catalyst, and dichloromethane. The reaction mixture is then heated and stirred. Dimethyl heptadec-8-enedioate and 2-butene are formed by metathesis of the 8-decenoic acid methyl ester and the 9-undecanoic methyl ester; the dimethyl heptadec-8-enedioate is then converted to heptadecanedioic acid following hydrogenation of the carbon-carbon double bond and hydrolysis of the methyl ester groups. While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method of making a dicarboxylic ester or acid, comprising:
    providing a reaction mixture comprising methyl 8-decenoate and a metathesis catalyst, wherein the methyl 8-decenoate is formed by an isomerizing methyl 9-decenoate, and wherein the yield of methyl 8-decenoate from the isomerizing is at least 50%;
    reacting the methyl 8-decenoate in the presence of the metathesis catalyst to form 1,16-dimethyl 8-hexadecenedioate; and
    hydrogenating the 1,16-dimethyl 8-hexadecenedioate to form 1,16-dimethyl hexadecanedioate.

2. The method of claim 1, further comprising converting the 1,16-dimethyl hexadecanedioate to hexadecanedioic acid.

* * * * *